(12) United States Patent
Getman

(10) Patent No.: US 11,832,872 B2
(45) Date of Patent: Dec. 5, 2023

(54) RESONATING PROBE WITH OPTIONAL SENSOR, EMITTER, AND/OR INJECTION CAPABILITY

(71) Applicant: Anya L. Getman, Sandy, OR (US)

(72) Inventor: Anya L. Getman, Sandy, OR (US)

( * ) Notice: Subject to any disclaimer, the term of this patent is extended or adjusted under 35 U.S.C. 154(b) by 776 days.

(21) Appl. No.: 16/832,574

(22) Filed: Mar. 27, 2020

(65) Prior Publication Data
US 2020/0305967 A1 Oct. 1, 2020

Related U.S. Application Data

(60) Provisional application No. 62/827,197, filed on Apr. 1, 2019.

(51) Int. Cl.
| | | |
|---|---|---|
| A61B 18/14 | (2006.01) | |
| A61B 18/22 | (2006.01) | |
| A61B 17/43 | (2006.01) | |
| A61B 18/00 | (2006.01) | |
| A61B 17/42 | (2006.01) | |

(52) U.S. Cl.
CPC .......... *A61B 18/1477* (2013.01); *A61B 17/43* (2013.01); *A61B 18/1485* (2013.01); *A61B 18/22* (2013.01); *A61B 2017/4216* (2013.01); *A61B 2018/00142* (2013.01); *A61B 2018/00154* (2013.01); *A61B 2018/00559* (2013.01); *A61B 2018/00964* (2013.01)

(58) Field of Classification Search
CPC ............ A61B 17/43; A61B 2017/4216; A61B 2018/00559
See application file for complete search history.

(56) References Cited

U.S. PATENT DOCUMENTS

| | | |
|---|---|---|
| 5,219,346 A | 6/1993 | Wagnieres et al. |
| 5,334,181 A | 8/1994 | Rubinsky et al. |
| 5,618,995 A | 4/1997 | Otto et al. |
| (Continued) | | |

FOREIGN PATENT DOCUMENTS

| | | |
|---|---|---|
| AU | 2012332233 B2 | 8/2017 |
| CN | 201905995 U | 7/2011 |
| (Continued) | | |

OTHER PUBLICATIONS

"A Surgical Cryoprobe for Targeted Transcorneal Freezing and Endothelial Cell Removal",(May 16, 2017), published on J Ophthalmol, v.2017, PMC5448072, 11 pages retrieved Sep. 27, 2021 from https://www.ncbi.nlm.nih.gov/pmc/articles/PMC5448072/, 11 pages.
(Continued)

*Primary Examiner* — Oommen Jacob
(74) *Attorney, Agent, or Firm* — Enterprise Patent LLC

(57) ABSTRACT

A microsurgical probe employs an optional probe support structure; an optical fiber for providing a feed path for an emission wavelength; a chemical feed path for delivering a chemical; a resonator motor; and a probe accessory tool. A microsurgical system additionally employs a sensor and an artificial intelligence (AI) system to assess conditions based on data provided by the sensor. The system can be employed to remove tumor tissue that is interwoven with healthy tissue. This system can also be employed to fertilize old, inflexible ova.

24 Claims, 8 Drawing Sheets

(56) References Cited

U.S. PATENT DOCUMENTS

| | | | |
|---|---|---|---|
| 5,627,922 A * | 5/1997 | Kopelman | B82Y 20/00 385/38 |
| 5,646,709 A | 7/1997 | Carter | |
| 6,322,578 B1 * | 11/2001 | Houle | A61B 17/2909 606/174 |
| 6,385,474 B1 | 5/2002 | Rather et al. | |
| 6,627,613 B2 | 9/2003 | Strobel | |
| 6,936,053 B1 * | 8/2005 | Weiss | A61F 9/007 604/117 |
| 7,527,624 B2 * | 5/2009 | Dubnack | A61F 9/00736 606/4 |
| 7,598,860 B2 | 10/2009 | Niemi | |
| 7,744,869 B2 | 6/2010 | Simon | |
| 7,851,758 B1 | 12/2010 | Scanlon et al. | |
| 7,854,511 B2 | 12/2010 | Molnar et al. | |
| 8,399,866 B2 | 3/2013 | Balakin | |
| 9,589,374 B1 | 3/2017 | Gao et al. | |
| 9,622,662 B2 | 4/2017 | Zuzak et al. | |
| 10,321,842 B2 | 6/2019 | Garten et al. | |
| 2002/0155601 A1 * | 10/2002 | Yan | C12N 5/0603 435/6.16 |
| 2003/0082798 A1 * | 5/2003 | Fortino | B01L 3/022 604/221 |
| 2004/0088748 A1 | 5/2004 | Perry | |
| 2005/0065436 A1 | 3/2005 | Ho et al. | |
| 2005/0246783 A1 * | 11/2005 | Christmann | A01K 67/0275 800/19 |
| 2012/0123193 A1 * | 5/2012 | Posillico | G01N 33/6848 250/282 |
| 2012/0283605 A1 | 11/2012 | Lewis | |
| 2013/0023052 A1 * | 1/2013 | Tanaka | G02B 21/32 435/461 |
| 2014/0223462 A1 | 8/2014 | Aimone et al. | |
| 2015/0164584 A1 | 6/2015 | Davalos et al. | |
| 2015/0256799 A1 | 9/2015 | Saggiomo et al. | |
| 2015/0335288 A1 | 11/2015 | Toth et al. | |
| 2017/0121660 A1 * | 5/2017 | Jinno | G02B 21/32 |
| 2017/0121736 A9 * | 5/2017 | Cohen | C12N 15/89 |
| 2018/0156881 A1 | 6/2018 | Poole et al. | |
| 2018/0164390 A1 | 6/2018 | Poole et al. | |
| 2018/0168527 A1 | 6/2018 | Poole et al. | |
| 2018/0224512 A1 | 8/2018 | Poole et al. | |
| 2019/0018096 A1 | 1/2019 | Poole et al. | |
| 2019/0042958 A1 * | 2/2019 | Letterie | G16H 30/40 |
| 2019/0053760 A1 | 2/2019 | Gerald | |
| 2019/0178962 A1 | 6/2019 | Poole et al. | |
| 2019/0336101 A1 | 11/2019 | Chiang et al. | |
| 2020/0305967 A1 * | 10/2020 | Getman | A61B 18/1485 |

FOREIGN PATENT DOCUMENTS

| | | |
|---|---|---|
| CN | 101386814 B | 4/2012 |
| CN | 204455111 U | 7/2015 |
| CN | 105854193 A | 8/2016 |
| EP | 1133334 B1 | 6/2006 |
| WO | WO8907468 A1 | 8/1989 |
| WO | 9639960 A1 | 12/1996 |
| WO | WO0163542 A1 | 8/2001 |
| WO | WO2005023121 A1 | 3/2005 |
| WO | 2008054487 A2 | 5/2008 |
| WO | 2009097220 A2 | 8/2009 |
| WO | WO2017079761 A1 | 5/2017 |

OTHER PUBLICATIONS

"Ablation for Arrhythmias" retrieved Sep. 27, 2021 from https://www.heart.org/en/health-topics/arrhythmia/prevention--treatment-of-arrhythmia/ablation-for-arrhythmias, 4 pages.

"Analysis of chromosome constitution of human spermatozoa with normal and aberrant head morphologies after Injection into mouse oocytes", Lee et al, (1996), Human Reproduction, vol. 11, No. 9, pp. 1942-1946.

"Autologous mitochondrial microinjection; a strategy to improve the oocyte quality and subsequent reproductive outcome during aging", Halimeh Mobarak et. al, (2019), 15 Pages.

"Caenorhabditis elegans" retrieved Sep. 27, 2021 from https://en.wikipedia.org/wiki/Caenorhabditis_elegans, 22 pages.

"Clinical Management of Epileptic Seizures in a Labrador retriever Dog", retrieved Feb. 7, 2020 from www.nexusacademicpublishers.com/table_contents_detail/13/91/html, p. 4.

"Colour" retrieved Sep. 27, 2021 from https://www.cs.mcgill.ca/~rwest/wikispeedia/wpcd/wp/c/Color.htm, 7 pages.

"Compatible Draeger Flow Sensor" retrieved Sep. 27, 2021 from https://www.cablesandsensors.com/products/compatible-draeger-flow-sensor-8403735?variant=33810255112, 5 pages.

"Contribution of human oocyte architecture to success of in vitro maturation technology", Khalili et al., (Jan. 2013), published on Iran J Reprod Med, v.11(1), PMC3941380, retrieved Sep. 27, 2021 from https://www.ncbi.nlm.nih.gov/pmc/articles/PMC3941380/, 10 pages.

"Datex Ohmeda" retrieved Sep. 27, 2021 from https://www.cablesandsensors.com/products/datex-ohmeda-compatible-disposable-temperature-probe-la003?variant=33809792520, 5 pages.

"Deep Learning Machine Vision texture inspection" retrieved Sep. 24, 2021 from https://www.youtube.com/watch?v=CUy2xQbRB-0, 3 pages.

"Development of a Handpiece and Probes for a Microsurgical Ultrasonic Aspirator: Instrumentation and Application", Yutaka Sawamura et al., (Dec. 1999), Neurosurgery, pp. 10.

"Effect of Purification of Bovine Serum Albumin on the Interaction of Human Semen with Mouse Ova in vitro", Quin et al, (1980), Biology of Reproduction 22, 134-140, pp. 7.

"Extra-abdominal desmoid tumors", Markhede et al., (Jul. 8, 2009), Acta Orthopaedica Scandinavica, 57:1, pp. 8.

"Fenbendazole Treatment May Influence Lipopolysaccharide Effects in Rat Brain", Randy L Hunter et al, (Oct. 2007), American Association for Laboratory Animal Science, pp. 6.

"Fertilization of human oocytes by microinjection of a single spermatozoon under the zona pellucida", Andrea Laws-King et al, (Oct. 1987), Fertility and Sterility, pp. 6.

"Gamma Probe-Assisted Brain Tumor Microsurgical Resection", Osvaldo et al, (2002), pp. 6.

"Generating Ultrasound with Piezo Components" retrieved Sep. 26, 2021 from https://www.piceramic.com/en/piezo-technology/generating-ultrasound-with-piezo-components/, 7 pages.

"Horse Wormer Guide", retrieved Feb. 7, 2020 from https://www.horse.com/content/wormer/horse-wormer-guide/, pp. 4.

"Intraoperative Fluorescence Imaging for Personalized Brain Tumor Resection", Belykh et al., (Oct. 17, 2016), pp. 27.

"Methods in cell biology", Shai, (Jan. 2, 2006), The Online Review of C. elegans Biology [Internet]. Pasadena (CA): WormBook; 2005-2018, 77 pages retrieved Sep. 27, 2021 from https://www.ncbi.nlm.nih.gov/books/NBK19784/, 77 pages.

"Microsurgical Probe" retrieved Sep. 27, 2021 from https://www.alibaba.com/trade/search?fsb=y&IndexArea=product_en&CatId=&SearchText=microsurgical+probe+, 5 pages.

"Miniaturized probe for femtosecond laser microsurgery and two photon imaging", Hoy et al., (Jul. 26, 2011), retrieved Sep. 26, 2021 from https://www.ncbi.nlm.nih.gov/pmc/articles/PMC3143712/, 13 pages.

"Oocyte Development" retrieved Sep. 27, 2021 from https://embryology.med.unsw.edu.au/embryology/index.php/Oocyte_Development, 17 pages.

"Open pulled straw (OPS) vitrification: A new way to reduce cryoinjuries of bovine ova and embryos", retrieved Feb. 6, 2020 from https://onlinelibrary.wiley.com/doi/abs/10.1002/(SICI)1098-2795(199809)51:1<53::AID-MRD6>3.0.CO;2-V, pp. 2.

"Outwitting the Blood-Brain Barrier", Neuwelt et al., (Nov. 15, 2016), Oncology Journal, vol. 30, Issue 11, pp. 6.

"Piezo Buzzers" retrieved Sep. 26, 2021 from https://www.americanpiezo.com/standard-products/buzzers.html, 4 pages.

"Piezoelectric driver finds buzzers resonant frequency", OZBEK, (Aug. 7, 2008), retrieved Sep. 26, 2021 from https://www.edn.com/piezoelectric-driver-finds-buzzers-resonant-frequency/, 2 pages.

(56) References Cited

OTHER PUBLICATIONS

"Piezoelectric Materials in RF Applications" retrieved Sep. 26, 2021 from https://www.intechopen.com/books/piezoelectric-materials/piezoelectric-materials-in-rf-applications, 33 pages.
"Quinoline and Benzimidazole Derivatives: Candidate Probes for In Vivo Imaging of Tau Pathology in Alzheimer's Disease", Nobuyuki Okamura et al., (Nov. 23, 2005), The Journal of Neuroscience, pp. 10857-10862.
"Resonance mode and sound pressure produced by circular diaphragms of electrostatic and piezoelectric speakers", Chiang et al., (Jan. 1, 2018), Applied Acoustics, vol. 129, pp. 365-378, retrieved Sep. 26, 2021 from https://www.sciencedirect.com/science/article/abs/pii/S0003682X17302712.
"Spermatid injection into human oocytes. I. Laboratory techniques and special features of zygote development", Tesarik et al., (1996), Human Reproduction, vol. 11, No. 4 , pp. 772-779.
"Surgery for brain tumours", retrieved Feb. 6, 2020 from https://www.cancerresearchuk.org/about-cancer/brain-tumours/treatment/surgery/remove-brain-tumour, p. 7.
"The Use of Sarmazenil in the Treatment of a Moxidectin Intoxication in a Foal", Muller et al., (2005), J Vet Intern Med; 19, pp. 348-349.
"The Van Andel Transparent Glass Microsurgical Cannula", Andel et al., (May 1, 1990), retrieved Sep. 27, 2021 from https://www.healio.com/ophthalmology/journals/osli/1990-5-21-5/%7B413cef68-33bb-43be-85fa-99ebf55e444a%7D/the-van-andel-transparent-glass-microsurgical-cannula, 3 pages.
"Toxocara canis infection in the paratenic host", (Jan. 31, 1998), Veterinary Parasitology, vol. 74, Issues 2-4 retrieved Feb. 7, 2020 from https://www.sciencedirect.com/science/article/abs/pii/S0304401797000861, pp. 2.
"Tumor cell expansion challenges current physics", University of Barcelona, (Sep. 25, 2018) retrieved Sep. 27, 2021 from https://www.sciencedaily.com/releases/2018/09/180925115223.htm, 4 pages.
NPL-38: "DJI Ronin-SC Gimbal Stabilizer" retrieved Sep. 14, 2021 from https://www.bhphotovideo.com/c/product/1492980-REG, 5 pages.
NPL-39: "How to Calculate Confidence Levels" retrieved Sep. 14, 2021 from https://sciencing.com/calculate-confidence-levels-2844.html, 6 pages.
NPL-40: "Is it possible to convert a mobile phone into a sonar device" retrieved Sep. 14, 2021 from https://www.quora.com/Is-it-possible-to-convert-a-mobile-phone-into-a-sonar-device, 3 pages.
NPL-41: "20 Portable Health Gadgets That Can Change Your Life" retrieved Sep. 14, 2021 from https://travelaway.me/portable-health-gadgets/, 25 pages.
NPL-42: "3rd International Symposium Current and Future Applications of Focused Ultrasound 2012" retrieved Sep. 15, 2021 from https://www.osa.org/en-us/meetings/global_calendar/events/2012/3rd_international_symposium_current_and_future_app/, 2 pages.
NPL-43: "5-Mode TENS Unit By Vive" retrieved Sep. 15, 2021 from https://www.youtube.com/watch?v=nd0TdjdEo8U, 3 pages.
NPL-44: "A concerning new study links miscarriages to cellphone radiation" retrieved Sep. 15, 2021 from https://www.vox.com/science-and-health/2018/2/15/17008482/cellphones-cancer-miscarriage-health, 6 pages.
NPL-45: "American Conference on Human Vibration" retrieved Sep. 14, 2021 from https://www.cdc.gov/niosh/mining/UserFiles/works/pdfs/2009-145.pdf, 147 pages.
NPL-46: "Ascariasis" retrieved Sep. 15, 2021 from https://www.mayoclinic.org/diseases-conditions/ascariasis/symptoms-causes/syc-20369593, 6 pages.
NPL-47: "Capacitive coupling" retrieved Sep. 14, 2021 from https://en.wikipedia.org/wiki/Capacitive_coupling, 3 pages.
NPL-48: "Clarius Portable Ultrasound" retrieved Sep. 15, 2021 from https://www.youtube.com/watch?v=ZHKXyG_CBxE, 3 pages.
NPL-49: (Abstract and Intro only) "Contact and non-contact ultrasonic measurement in the food industry" retrieved Sep. 14, 2021 from https://www.researchgate.net/publication/285546493_Contact_and_non-contact_ultrasonic_measurement_in_the_food_industry_A_review, 10 pages.
NPL-50: "da Vinci Surgical System" retrieved Sep. 14, 2021 from https://en.wikipedia.org/wiki/Da_Vinci_Surgical_System, 4 pages.
NPL-51: "Doctors identify brain abnormalities in U.S. Embassy victims from Cuba attack" retrieved Sep. 15, 2021 from https://www.nbcnews.com/news/us-news/doctors-identify-brain-abnormalities-u-s-embassy-victims-cuba-attack-n826996, 7 pages.
NPL-52: "Draganfly to deploy drones to detect coughing, signs of infection" retrieved Sep. 15, 2021 from https://www.fierceelectronics.com/electronics/draganfly-to-deploy-drones-to-detect-coughing-signs-infection, 4 pages.
NPL-53: "Functional magnetic resonance imaging" retrieved Sep. 14, 2021 from https://en.wikipedia.org/wiki/Functional_magnetic_resonance_imaging, 28 pages.
NPL-54: "Gamma 40Hz Light Therapy Kit" retrieved Sep. 14, 2021 from https://gammalighttherapy.com/collections/40hz-light-devices/products/gamma-40-hz-light-therapy-kit, 5 pages.
NPL-55: "Handheld Tens Unit" retrieved Sep. 14, 2021 from https://www.bing.com/shop?q=handheld+tens+unit&qs=n&form=SHOPSB&sp=-1&pq=handheld+tens+unit&sc=0-18&sk=&cvid=5E57EA01AEB34F4EAF0E946E67363840, 1 Page.
NPL-56: "Handheld ultrasound devices" retrieved Sep. 16, 2021 from https://www.bing.com/shop?q=handheld+ultrasound+devices&FORM=SHOPPA&originIGUID=E018626F2D6B4C4B98E5335F6F8F51BA, 1 page.
NPL-57: "How to Make Piezoelectric Crystal Speaker" retrieved Sep. 15, 2021 from https://www.youtube.com/watch?v=R7zjfaPKMSE, 4 pages.
NPL-58: "How to Move Things with Sound" retrieved Sep. 15, 2021 from https://www.youtube.com/watch?v=L5fVFA2sWt4, 5 pages.
NPL-59: "IL426 Subcutaneous Self injection for anti-coagulation treatment" retrieved Sep. 14, 2021 from https://www.qegateshead.nhs.uk/sites/default/files/users/user53/gynaeoncology/IL426%20Subcutaneous%20Self%20injection%20for%20anti-coagulation%20treatment.pdf, 4 pages.
NPL-60: "Implantable cardioverter-defibrillator" retrieved Sep. 14, 2021 from https://en.wikipedia.org/wiki/Implantable_cardioverter-defibrillator, 9 pages.
NPL-61: "Inductive charging" retrieved Sep. 14, 2021 from https://en.wikipedia.org/wiki/Inductive_charging, 14 pages.
NPL-62: "IR Wireless" retrieved Sep. 14, 2021 from https://searchmobilecomputing.techtarget.com/definition/IR-wireless, 3 pages.
NPL-63: "Jet Injector" retrieved Sep. 14, 2021 from https://en.wikipedia.org/wiki/Jet_injector, 8 pages.
NPL-64: "Magnasonic LED Pocket Pico Video Projector" retrieved Sep. 14, 2021 from https://www.amazon.com/Magnasonic-Rechargeable-Hi-Resolution-Presentations-PP60/dp/B016N98GG6, 11 pages.
NPL-65: "Mu-Metal—Amorphous Magnetic shielding materials" retrieved Sep. 15, 2021 from https://web.archive.org/web/20180815085309/https://hollandshielding.com/Mu-Metal-Amorphous-Magnetic-shielding-materials, which is the web archive of https://hollandshielding.com/Mu-Metal-Amorphous-Magnetic-shielding-materials from Aug. 15, 2018, 1 page.
NPL-88: "Traumatic bleeding stopped cold using snake venom" retrieved Sep. 15, 2021 from https://www.dailykos.com/stories/2021/7/17/2040356/-Traumatic-bleeding-stopped-cold-using-snake-venom-visible-light-and-some-cool-chemistry, 29 pages.
NPL-89: "Tubular photo sensor" retrieved Sep. 14, 2021 from https://www.automationdirect.com/adc/shopping/catalog/sensors_-z-_encoders/photoelectric_sensors/18mm_round_-_nonmetal/through_beam_(ss_-z-_fa_-z-_fb_series)/fald-pp-0a?gclid=Cj0KCQjwsYb0BRCOARIsAHbLPhEFRYCJVQQeFff75GpkSOBNEUiGQ-qkdV0NYAAtlqoCprp0KGo2XlwaAhTuEALw_wcB, 4 pages.
NPL-90: (Abstract only) "Ultrasonic detection of bone fragment in mechanically deboned chicken breasts" retrieved Sep. 14, 2021 from https://www.researchgate.net/publication/222428475_Ultrasonic_detection_of_bone_fragment_in_mechanically_deboned_chicken_breasts, 7 pages.
NPL-91: "Ultrasound Scans of Your Baby Now Available Via Smartphone" retrieved Sep. 14, 2021 from https://www.fastcompany.com/1725155/ultrasound-scans-your-baby-now-available-smartphone, 4 pages.

(56) References Cited

OTHER PUBLICATIONS

NPL-92: "Whole body vibration" retrieved Sep. 14, 2021 from https://en.wikipedia.org/wiki/Whole_body_vibration, 11 pages.
NPL-93: "Wireless power transfer" retrieved Sep. 14, 2021 from https://en.wikipedia.org/wiki/Wireless_power_transfer, 29 pages.
NPL-94: "WVU Rockefeller Neuroscience team first to use ultrasound to treat Alzheimers" retrieved Sep. 15, 2021 from https://www.wvnews.com/statejournal/news/historic-breakthrough-wvu-rockefeller-neuroscience-team-first-to-use-ultrasound/article_b9951ba2-19ba-54ba-8e1c-0096fb4824bc.html, 5 pages.
NPL95: "Robot Trajectory Control Employing a Novel Neural Architecture," Getman, Anna L., Engineering Masters Thesis: Rensselaer Polytechnic Institute, Troy, NY, Dec. 1992.
NPL96: Abstract Only "Low conductivity on electrical properties tomography demonstrates unique tumor habitats indicating progression in glioblastoma" Park et al. Eur Radiol. 31(12):9675 (Dec. 2021) https://pubmed.ncbi.nlm.nih.gov/33880619/ Downloaded Jun. 2, 2021.
NPL97: Abstract Only "Minimally Invasive Electrical Impedance Measurements of Ovum Exemplified Using Microelectrodes" Lui et al. 2nd IEEE International Conference on Nano/Micro Engineered and Molecular Systems (Jan. 2007) https://ieeexplore.ieee.org/document/4160517 Downloaded Jun. 2, 2023.
NPL-66: "New wonder diagnosis handheld medical scanner" retrieved Sep. 15, 2021 from https://www.youtube.com/watch?v=TdyK0ko6igU, 3 pages.
NPL-67: "Omnicoffeelid Premium Omnieye Coffee Lid Camera" retrieved Sep. 14, 2021 from https://www.ebay.com/p/23005320855?_trkparms=aid%3D333200%26algo%3DCOMP.MBE%26ao%3D1%26asc%3D20170706093515%26meid%3D636186d2f5d4472088719a98aa686646%26pid%3D100831%26rk%3D1%26rkt%3D3%26itm%3D371732528776%26pmt%3D1%26noa%3D1%26pg%3D2322090&_trksid=p2322090.c100831.m5025&iid=371732528776, 2 pages.
NPL-68: "Oxymap" retrieved Sep. 15, 2021 from https://www.oxymap.com/, 2 pages.
NPL-69: "Parasitic Worms in Humans: Know the Facts" retrieved Sep. 15, 2021 from https://www.healthline.com/health/worms-in-humans, 12 pages.
NPL-70: "PDT 4Colors LED Light Photodynamic Facial Skin Care" www.wish.com. Sep. 14, 2021, 3 pages.
NPL-71: "Philips HeartStart Home AED Defibrillator Value Package with Slim Carry Case" retrieved Sep. 14, 2021 from https://www.amazon.com/HeartStart-861284-Philips-Home-Defibrillator/dp/B00064CED6, 9 pages.
NPL-72: "Physics of magnetic resonance imaging" retrieved Sep. 14, 2021 from https://en.wikipedia.org/wiki/Physics_of_magnetic_resonance_imaging, 18 pages.
NPL-73: "Proteus" retrieved Sep. 14, 2021 from https://proteus.ac.uk/, 2 pages.
NPL-74: (Abstract only) "Retinal Oximetry Imaging in Alzheimer's Disease" retrieved Sep. 15, 2021 from https://pubmed.ncbi.nlm.nih.gov/26444785/, 2 pages.
NPL-75: "Retinal Oximetry" retrieved Sep. 15, 2021 from https://eyewiki.aao.org/Retinal_Oximetry, 4 pages.
NPL-76: "RF exposure to Humans, and much more" retrieved Sep. 14, 2021 from https://wade4wireless.com/2014/02/01/rf-exposure-to-humans-and-much-more/, 6 pages.
NPL-77: "Saving Sudden Cardiac Arrest Victims in the Workplace" retrieved Sep. 15, 2021 from https://web.archive.org/web/20191201171943/https://www.osha.gov/Publications/3185.html, which is the web archive of https://www.osha.gov/Publications/3185.html from Dec. 1, 2019.
NPL-78: "So How Exactly Does a GIF Cause a Seizure" retrieved Sep. 15, 2021 from https://t.co/X4nR7dKS4J, 10 pages.
NPL-79: "Super small Φ4mm 650nm 0.5mw 1mw 5mw Red dot laser module Miniature laser head" reineved Sep. 14, 2021, www.civillaser.com, 5 pages.
NPL-80: "Supercapacitor" retrieved Sep. 14, 2021 from https://en.wikipedia.org/wiki/Supercapacitor, 53 pages.
NPL-81: "The LTP-50 Cold Laser Therapy Pen" retrieved Sep. 14, 2021 from https://energyhealersteve.com/product/cold-laser-therapy-pen-ltp-50/?dTribesID=92a314379b6da2f239adda1ae654eee7%7Cadtribes%7C3283&utm_source=Google%20Shopping&utm_campaign=cold%20laser&utm_medium=cpc&utm_term=3283&gclid=Cj0KCQjwsYb0BRCOARIsAHbLPhF_SL6IE66VBKR0S0R2qoza8KPW2J6Oq7UaSHPWH59nQyXkn6OTgdlaAlzFEALw_wcB, 5 pages.
NPL-82: "The Mysteries of IP65, IP66, and IP67 Rated Enclosures Explained" retrieved Sep. 14, 2021 from http://www.budind.com/blog/2014/02/the-mysteries-of-ip-rated-enclosures-explained/, 6 pages.
NPL-83: "The use of seat effective amplitude transmissibility (SEAT) values to predict dynamic seat comfort" retrieved Sep. 14, 2021 from https://www.semanticscholar.org/paper/The-use-of-seat-effective-amplitude-(SEAT)-values-Niekerk-Pielemeier/f9385950e17b583a04338be68a3b4e05db2c6b09, 3 pages.
NPL-84: "The Worlds first portable Auto Defibrillator" retrieved Sep. 15, 2021 from https://www.youtube.com/watch?v=-Be60EPaqCs, 3 pages.
NPL-85: "Timer Oscillator Kit" retrieved Sep. 14, 2021 from https://store.synthrotek.com/555_Timer_Oscillator_Kit, 5 pages.
NPL-86: "TP-Link AC750 Wireless Portable Nano Travel Router" retrieved Sep. 14, 2021 from https://www.amazon.com/TP-Link-Wireless-Portable-Travel-Router/dp/B07V2R7W11/, 9 pages.
NPL-87: "Transducer for HIFU High intensity focus ultrasound" Sep. 15, 2021 www.alibaba.com, 7 pages.

* cited by examiner

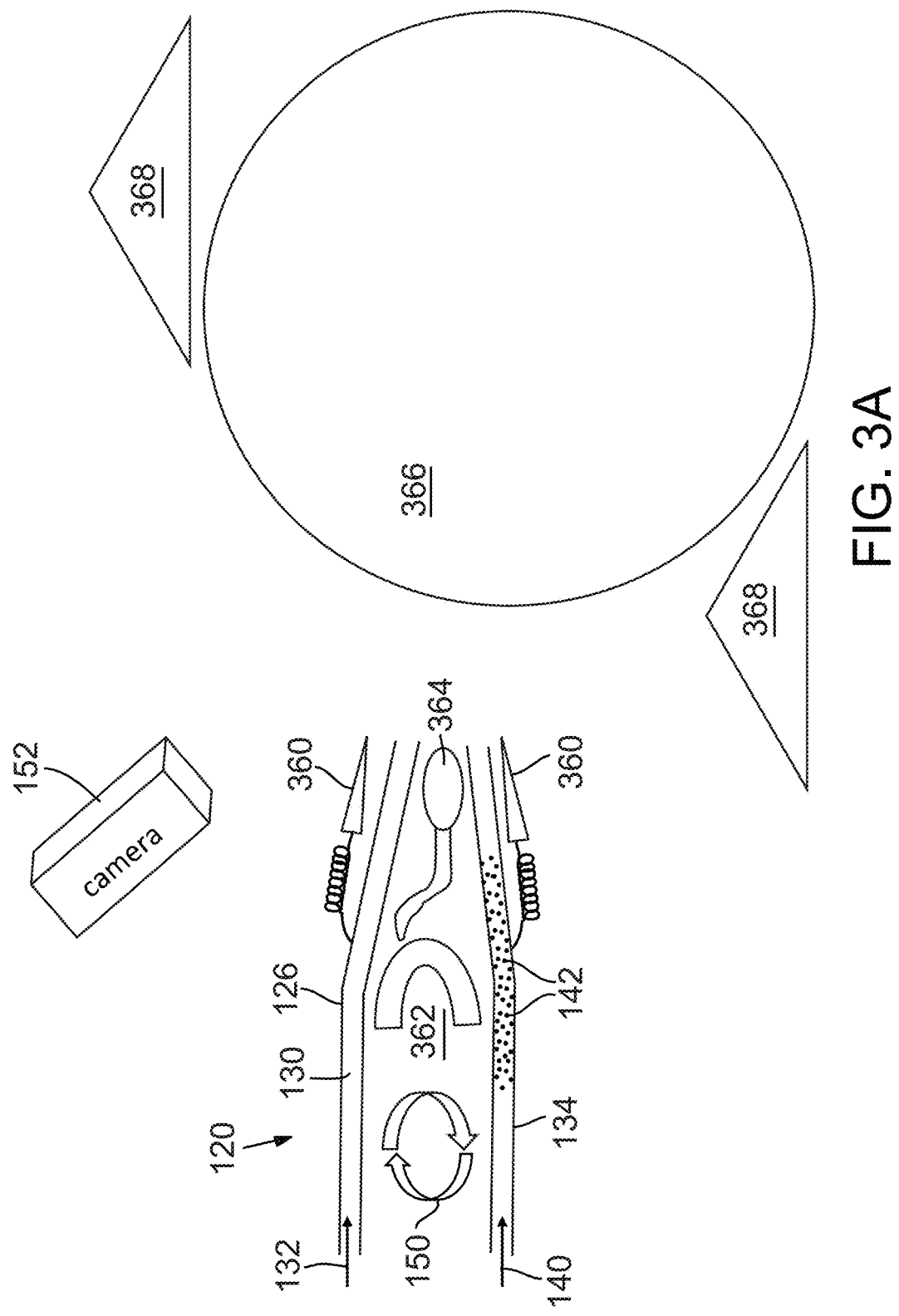

RESONATING PROBE WITH OPTIONAL SENSOR, EMITTER, AND/OR INJECTION CAPABILITY

CROSS REFERENCE TO RELATED APPLICATION

This application is a non-provisional application of U.S. Provisional Application No. 62/827,197, which was filed on Apr. 1, 2019, the contents of which are herein incorporated by reference in their entirety for all purposes.

TECHNICAL FIELD

The field of this disclosure relates generally to microsurgical probes and, in particular, to methods and systems employing a microsurgical resonating probe with a chemical dispensing capability and optionally one or more tools that can be engaged for specific tasks such as for tumor removal or intracytoplasmic sperm injection (ICSI).

BACKGROUND INFORMATION

Present medical technology employs freezing or cryogenic techniques to treat tumors. Some examples include Chinese Pat. Pub. No. CN 201905995, U.S. Pat. No. 5,334,181, and U.S. Pat. Pub. No. 2015/0164584. Despite these advances, many tumors that are interwoven with healthy tissue are considered inoperable or untreatable.

In vitro fertilization (IVF) is a process in which hundreds of sperm are introduced near an egg to permit one of them to penetrate the egg. Present artificial insemination techniques may, however, involve intracytoplasmic sperm injection (ICSI). ICSI involves the direct injection of sperm into an ovum (egg) (or ova (eggs)). Contemporary sperm injection procedures are performed under a microscope using multiple micromanipulation devices. A holding pipette stabilizes an egg with gentle suction. From the opposite side, a thin glass micropipette is used pierce the egg to inject a sperm cell into the cytoplasm of the egg. Prior to injection, this micropipette is used to collect a single immobilized sperm, which has been immobilized by cutting its tail with the point of the micropipette. See Chinese Patent No. CN 204455111 and CN 101386814. These methods of ICSI have continued to evolve and now include computer controlled piezo manipulation systems and robotics.

Despite these advances in ICSI methods, older mammalian eggs, such as those of women or mares, are typically brittle and less flexible to incursions. This means that they have a tendency to lyse or burst (pop) during ICSI procedures or even during IVF procedures.

OVERVIEW OF DISCLOSURE

One aspect of this disclosure relates to microsurgical probes and, in particular, to methods and systems employing a microsurgical resonating probe with chemical dispensing capability and one or more tools that can be engaged specific tasks such as for tumor removal or intracytoplasmic sperm injection (ICSI).

In some embodiments, a microsurgical probe comprises an optional probe support structure; an optical fiber for providing a feed path for an emission wavelength; a chemical feed path for delivering a chemical; a resonator motor; and a probe accessory tool.

In some additional, alternative, or selectively cumulative embodiments, a microsurgical system comprises an optional probe support structure; an optical fiber for providing a feed path for an emission wavelength; a chemical feed path for delivering a chemical; a resonator motor; a probe accessory tool; a sensor; an artificial intelligence (AI) system to assess conditions based on data provided by the sensor.

In some additional, alternative, or selectively cumulative embodiments, a method for removing tumor tissue comprises optionally pretreating the tumor tissue with a chemical; employing a wavelength emitter and a sensor to guide a microsurgical probe to the tumor tissue; employing the probe to freeze the tumor tissue; employing the probe to lubricate the tumor tissue; employing the probe to resonate the tumor tissue; determining readiness of the tumor tissue for removal; and employing a tool associated with the probe to grasp the tumor tissue.

In some additional, alternative, or selectively cumulative embodiments, a method for fertilizing an ovum (or egg) comprises optionally pretreating the ovum with a chemical; employing a wavelength emitter and a sensor to guide a microsurgical probe in proximity to the ovum; employing the probe to supply a softener to an outer surface of the ovum; employing the probe to resonate the tumor tissue; evaluating potential sperm injection points; and employing a tool associated with the probe to penetrate the outer surface of the ovum and inject a sperm into the ovum.

In some additional, alternative, or selectively cumulative embodiments, a method for fertilizing an ovum (or egg) comprises employing an injection needle controller to control the location and angle of injection, the rate and alternation of needle approach and retreat, the rate and modes of resonant vibration of the needle, and the rate of sperm injection.

In some additional, alternative, or selectively cumulative embodiments, the chemical comprises a tumor-shrinking chemical.

In some additional, alternative, or selectively cumulative embodiments, the chemical comprises a lubricating chemical.

In some additional, alternative, or selectively cumulative embodiments, the chemical comprises a temperature-adjusting chemical.

In some additional, alternative, or selectively cumulative embodiments, the chemical comprises a de-wormer.

In some additional, alternative, or selectively cumulative embodiments, the chemical is capable of crossing the blood-brain barrier.

In some additional, alternative, or selectively cumulative embodiments, the chemical comprises Taurolidine or Taurultam.

In some additional, alternative, or selectively cumulative embodiments, the resonator comprises an adaptive resonator.

In some additional, alternative, or selectively cumulative embodiments, the resonator comprises an adaptively unbalanced resonator.

In some additional, alternative, or selectively cumulative embodiments, the probe accessory tool comprises a grasping tool.

In some additional, alternative, or selectively cumulative embodiments, the probe accessory tool comprises a scraping tool.

In some additional, alternative, or selectively cumulative embodiments, the probe accessory tool comprises a suction tool.

In some additional, alternative, or selectively cumulative embodiments, the probe accessory tool comprises a hollow needle.

In some additional, alternative, or selectively cumulative embodiments, the probe accessory tool comprises a semicircular, beveled or angled hollow needle.

In some additional, alternative, or selectively cumulative embodiments, the probe accessory tool comprises a sperm coaxing actuator. Sometimes sperm have lost mobility during invitro manipulation processes and require external means of locomotion to reach their target (the ovum).

In some additional, alternative, or selectively cumulative embodiments, the probe accessory tool is operable to be flash temperature adjusted, by means of a chemical or power source.

In some additional, alternative, or selectively cumulative embodiments, in the probe accessory tool is operable to be flash cooled using chemicals or power sources.

In some additional, alternative, or selectively cumulative embodiments, the probe accessory tool is operable to be flash heated, using chemicals or power sources.

In some additional, alternative, or selectively cumulative embodiments, the chemical includes a radioisotope.

In some additional, alternative, or selectively cumulative embodiments, the wavelength emitter is a gamma probe.

In some additional, alternative, or selectively cumulative embodiments, the emission wavelength comprises light, emitted via laser beam.

In some additional, alternative, or selectively cumulative embodiments, the emission wavelength comprises UV light.

In some additional, alternative, or selectively cumulative embodiments, the emission wavelength comprises visible light.

In some additional, alternative, or selectively cumulative embodiments, the emission wavelength comprises infrared light.

In some additional, alternative, or selectively cumulative embodiments, the emission wavelength comprises sound.

In some additional, alternative, or selectively cumulative embodiments, the emission wavelength comprises audible sound.

In some additional, alternative, or selectively cumulative embodiments, the emission wavelength comprises ultrasound.

In some additional, alternative, or selectively cumulative embodiments, the emission wavelength comprises radio waves.

In some additional, alternative, or selectively cumulative embodiments, the sensor is an image sensor.

In some additional, alternative, or selectively cumulative embodiments, the sensor comprises a sound sensor.

In some additional, alternative, or selectively cumulative embodiments, the tumor tissue is interwoven with healthy tissue.

In some additional, alternative, or selectively cumulative embodiments, the tumor tissue is located in the brain.

In some additional, alternative, or selectively cumulative embodiments, the probe comprises a flash chill tip.

In some additional, alternative, or selectively cumulative embodiments, the lubricant attaches to a colder surface of adjacent bodies.

In some additional, alternative, or selectively cumulative embodiments, the lubricant distributes in a thin coat.

In some additional, alternative, or selectively cumulative embodiments, the resonator causes tumor tissue to loosen from healthy tissue.

In some additional, alternative, or selectively cumulative embodiments, the probe is capable of cauterizing bleeding.

In some additional, alternative, or selectively cumulative embodiments, the ovum is older than 30 years.

In some additional, alternative, or selectively cumulative embodiments, the ovum is susceptible to popping.

In some additional, alternative, or selectively cumulative embodiments, the ovum has a coat that exhibits reduced flexibility.

In some additional, alternative, or selectively cumulative embodiments, the ovum is a mammalian ovum.

In some additional, alternative, or selectively cumulative embodiments, the ovum is a horse ovum.

In some additional, alternative, or selectively cumulative embodiments, the ovum is a human ovum.

In some additional, alternative, or selectively cumulative embodiments, operation of the tool is subject to feedback control.

In some additional, alternative, or selectively cumulative embodiments, an artificial intelligence (AI) system assists in operation of the tool.

In some additional, alternative, or selectively cumulative embodiments, an artificial intelligence (AI) system identifies when tumor periphery is adequately lubricated.

In some additional, alternative, or selectively cumulative embodiments, an artificial intelligence (AI) system identifies when resonance has adequately loosened tumor tissue before grasping is performed with the tool.

In some additional, alternative, or selectively cumulative embodiments, an artificial intelligence (AI) system identifies and bleeding regions for cauterization.

In some additional, alternative, or selectively cumulative embodiments, an artificial intelligence (AI) system identifies when the outer surface of the ovum is adequately lubricated.

In some additional, alternative, or selectively cumulative embodiments, an artificial intelligence (AI) system identifies when a trial press to a location along the outer surface of the ovum is least vulnerable to popping.

In some additional, alternative, or selectively cumulative embodiments, an artificial intelligence (AI) system identifies when resonance has adequately allowed for a safe injection and subsequent removal.

In some additional, alternative, or selectively cumulative embodiments, an injection needle controller controls the location and angle of injection, the rate and alternation of needle approach and retreat, the rate and modes of resonant vibration of the needle, the rate of sperm injection.

In some additional, alternative, or selectively cumulative embodiments, visual, chemical, and/or needle force feedback (such as measured by spring force and compression) are compared to database references to determine the degree of risk of ovum membrane bursting.

In some additional, alternative, or selectively cumulative embodiments, multiple candidate injection sites are test pressed and vibrated before an actual injection is attempted.

In some additional, alternative, or selectively cumulative embodiments, ovum itself might be rotated, loosened, or compressed in its holding device as test sites are evaluated.

In some additional, alternative, or selectively cumulative embodiments, membrane softening agent concentration can be actively varied during test presses or during the actual injection.

In some additional, alternative, or selectively cumulative embodiments, the actuator can optionally apply a sealant or adhesive to glue or to tape small cuts located at the site of the tumor removal.

In some additional, alternative, or selectively cumulative embodiments, the controller monitors perceived damage to the healthy tissue that is interwoven with the tumor, and if a threshold is crossed, the controller may change parameters to mitigate the damage.

In some additional, alternative, or selectively cumulative embodiments, the site of tumor removal can be chilled to reduce damage from the swelling of the healthy tissue that is interwoven with the tumor.

Selectively cumulative embodiments are embodiments that include any combination of multiple embodiments that are not mutually exclusive.

Additional aspects and advantages will be apparent from the following detailed description of example embodiments, which proceeds with reference to the accompanying drawings.

BRIEF DESCRIPTION OF THE DRAWINGS

FIG. 3A illustrates an embodiment of a microsurgical probe suitable for fertilizing an ovum that is susceptible to bursting.

DETAILED DESCRIPTION OF EMBODIMENTS

Figure 1A:
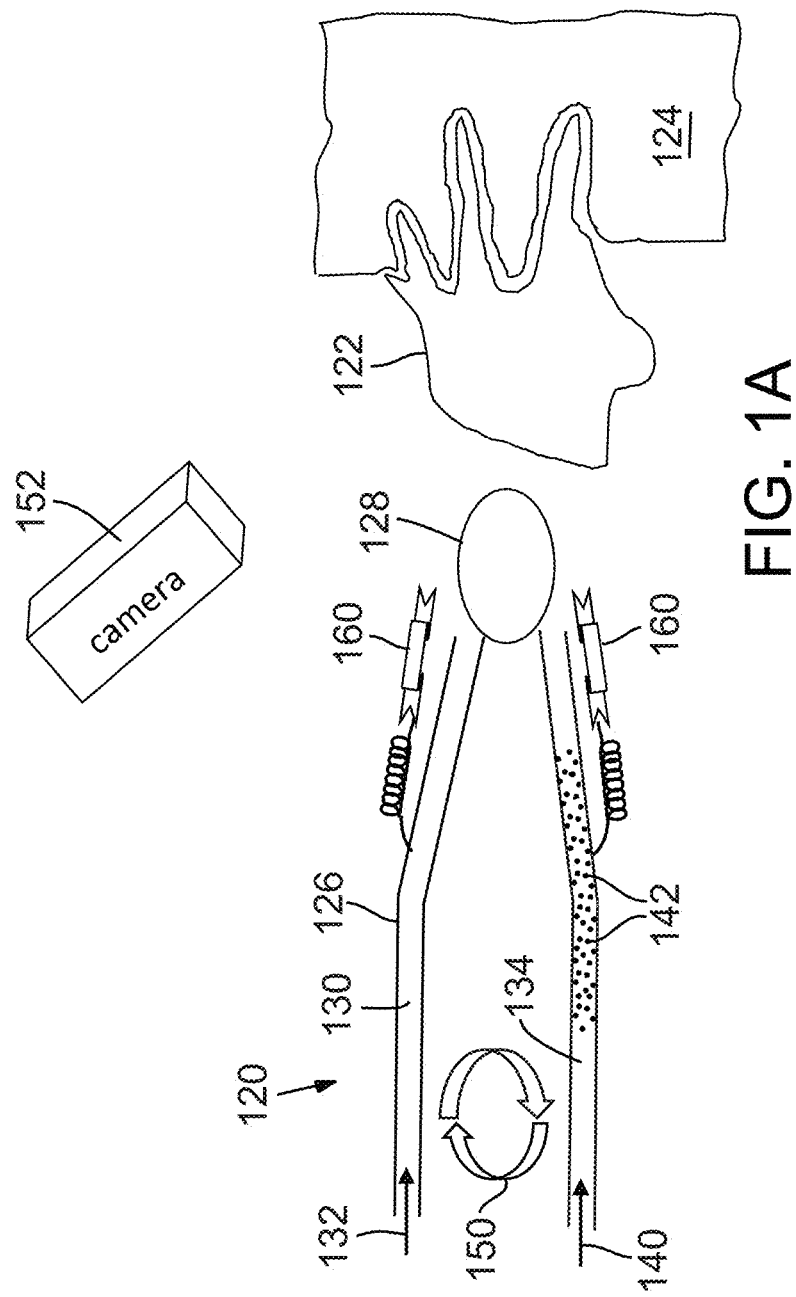
FIG. 1A illustrates an embodiment of a microsurgical probe suitable for removing a tumor that is interwoven with healthy tissue.

Example embodiments are described below with reference to the accompanying drawings. Unless otherwise expressly stated in the drawings, the sizes, positions, etc., of components, features, elements, etc., as well as any distances therebetween, are not necessarily to scale, and may be disproportionate and/or exaggerated for clarity.

The terminology used herein is for the purpose of describing particular example embodiments only and is not intended to be limiting. As used herein, the singular forms "a," "an" and "the" are intended to include the plural forms as well, unless the context clearly indicates otherwise. It should be recognized that the terms "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween. Unless indicated otherwise, terms such as "first," "second," etc., are only used to distinguish one element from another. For example, one element could be termed a "first element" and similarly, another element could be termed a "second element," or vice versa. The section headings used herein are for organizational purposes only and are not to be construed as limiting the subject matter described.

Unless indicated otherwise, the terms "about," "thereabout," "substantially," etc. mean that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art.

Spatially relative terms, such as "right," left," "below," "beneath," "lower," "above," and "upper," and the like, may be used herein for ease of description to describe one element's or feature's relationship to another element or feature, as illustrated in the drawings. It should be recognized that the spatially relative terms are intended to encompass different orientations in addition to the orientation depicted in the figures. For example, if an object in the figures is turned over, elements described as "below" or "beneath" other elements or features would then be oriented "above" the other elements or features. Thus, the exemplary term "below" can, for example, encompass both an orientation of above and below. An object may be otherwise oriented (e.g., rotated 90 degrees or at other orientations) and the spatially relative descriptors used herein may be interpreted accordingly.

Unless clearly indicated otherwise, all connections and all operative connections may be direct or indirect. Similarly, unless clearly indicated otherwise, all connections and all operative connections may be rigid or non-rigid.

Like numbers refer to like elements throughout. Thus, the same or similar numbers may be described with reference to other drawings even if they are neither mentioned nor described in the corresponding drawing. Also, even elements that are not denoted by reference numbers may be described with reference to other drawings.

Many different forms and embodiments are possible without deviating from the spirit and teachings of this disclosure and so this disclosure should not be construed as limited to the example embodiments set forth herein.

Many tumors that are interwoven with healthy tissue are currently considered inoperable or untreatable, such as desmoid tumors or brain tumors. In many cases, the tumors are not dense enough to be extracted, or the extraction would cause too much damage to the surrounding healthy tissue. In addition, tools for microsurgical techniques are limited because they can tend to do only one or perhaps two things well. Some microsurgical tools include blades for scraping out a tumor. Other microsurgical tools are employed to extract tumors from healthy tissue by use of tubular retractor systems. However, the use of these tools in removal of tumors may cause retractor-associated injury. Moreover, these same tools do not incorporate grasping or suctioning features to effect tumor removal.

FIG. 1A illustrates an embodiment of a microsurgical probe 120 suitable for removing tumor tissue 122 that may be interwoven with healthy tissue 124, such as part of a brain stem, a muscle, a bone mass, a nerve fiber, or an organ. In particular, tumors can be interwoven with healthy tissue, including but not limited to connective and epithelial tissues, endothelium, mesothelium, blood and lymphoid cells, smooth and striated muscle, the APUD system, other neural crest-derived cells, as well as benign tumors.

With reference to FIG. 1A, the microsurgical probe 120 includes an optional probe support structure 126, one or more optical fibers 126 for providing respective feed path 130 for emission wavelengths of light 132, and one or more chemical feed paths 134 for delivering one or more chemicals 142 in respective flow directions 140. The microsurgical probe 120 may also include one or more resonator motors 150 and one or more probe accessory tools 160. In some embodiments, the microsurgical probe 120 may cooperate with one or more sensors 152 and/or a software processing system that may employ an artificial intelligence (AI) system to assess conditions based on data provided by the sensor(s) 152.

The probe support structure 126 may be cylindrical or have other cross-sectional shape, such as elliptical, oval, hexagonal, octagonal, star-shaped, or other polygonal shape. In some embodiments, the optical fiber 130 and the chemical feed path 140 may provide some or all the probe support structure 126. For example, the optical fiber 130 and the chemical feed path 140 can form part of an outer housing of the microsurgical probe 120. In other embodiments, these features may be attached to the probe structure 126, such as between the points of a cross-sectional star shape or attached to the flat surfaces of a cross-sectional hexagonal shape.

The microsurgical probe 120 or its probe support structure 126 may be made of glass, metals, plastics, or polymers, or any combination thereof. Glass examples include the Van Andel transparent glass microsurgical cannula, which is a disposable 21-gauge transparent glass cannula that provides optimal visual control of aspiration-irrigation procedures in cataract surgery and iris repair. Metal examples include stainless steel and tungsten carbide. Plastics or polymers examples include polyvinyl chloride and thermoplastic polyurethane. However, any suitable material or any combination of suitable materials can be employed. For examples, some suitable materials include FDA-approved materials for use inside the human body, such as Noryl™. Other suitable materials might include materials that can be utilized in 3D printers, such as materials used in fused deposition modeling (FDM), digital light processing (DLP), or stereolithography (SLA) printers. Conventional consumer FDM printers can provide a layer thickness of 0.2 or 0.3 mm. Some better desktop models even claim a vertical resolution of 0.02 mm. Readily available SLA printers such can provide layers as thin as 0.025 mm. More advanced SLA printers can offer a 25-micron XY resolution and 25-300 microns (user selectable) in the Z, using an 85-micron laser. The actual accuracy may depend on many factors such as the print performance of an individual 3D printing resin.

While 3D printing is an example of one manufacturing method, any suitable manufacturing method may be employed. Other manufacturing techniques may include extrusion, reinforced hosing and coiled tubing. The components of such tubing can include a variety of materials that allow for tubing flexibility and pressure tolerance. These materials may include nylon, polyurethane (as well as polyurethane flexible plastic), polyethylene, polypropylene, and polyvinyl chloride. These techniques may form the microsurgical probe 120 or its probe support structure 126 as single production piece, or these techniques may be employed to produce the microsurgical probe 120 or its probe support structure 126 as two or more pieces that are subsequently connected.

The optical fiber 130 may utilize any conventionally suitable optical fiber material and may be formed as part of the microsurgical probe 120 or its probe support structure 126. For examples, some suitable materials include FDA-approved materials for use inside the human body. Examples of fibers used include those used in a fiber optic LED ear otoscope. The emission wavelengths of radiation to be propagated by these optical fibers 130 may influence the choice of the fiber materials employed.

The emission wavelengths may be selected for lighting so that the sensors 152 can detect or distinguish tissues. The emission wavelengths may be selected for removing tissue, such as by ablation, melting, or interacting with chemicals to dissolve tissue. The emission wavelengths may be selected for tissue repair, such as for cauterizing wounds, acting as a catalyst for a chemical reaction, or enhancing selective permeability for certain types of molecules, proteins, microstructures, or microorganisms to penetrate a selected organic target.

The optical fiber 130 may be configured to propagate multiple emission wavelengths, either individually or simultaneously. The optical fiber 130 may be configured to propagate multiple emission wavelengths, either individually or simultaneously. Exemplary wavelengths include the visible spectrum, 400-700 nm, the ultraviolet spectrum, 10-400 nm, the infrared spectrum, 700 nm-1 mm, the x-ray spectrum, 0.01 to 10 nanometers, and the gamma-ray spectrum, <10 µm. Laser sources for these wavelengths are readily available. Typical emission wavelengths may range from UV to IR. For example, visible wavelengths may be employed for lighting and IR wavelengths may be employed for tissue ablation and/or cauterization. One will appreciate that laser wavelengths from the UV to the IR have been used for tissue ablation with a variety of repetition rates and pulsewidths. In one example, a 780 nm femtosecond laser may be employed through an air-core photonic crystal optical fiber 30 fiber for surgical applications. A similar laser may also be used as a basis for two-photon microscopy. See https://www.ncbi.nlm.nih.gov/pmc/articles/PMC3143712/.

However, one will appreciate that other wavelengths may be employed for imaging and tissue manipulation. For example, a gamma probe technique uses the sodium phytate technetium as a tracer and inguinal scanning with probe to identify penile carcinoma. See http://www.scielo.br/scielo.php?script=sci_arttext&pid=S1677-55382007000100009). Also, radiofrequency energy (similar to microwave heat) may be used to destroy a small area of tumor tissue 122.

The chemical feed paths 134 can be configured to support delivery of a variety of biological agents or chemicals 142. The configuration may include the cross-sectional dimensions of the feed path 134, the material employed to construct the feed path 134, and/or any treatment of the internal or external walls of the feed path 134.

Chemicals 142 may include one or more of a shrinking agent, a lubricant, a sealant, an adhesive, an anti-cancer agent, and an anti-bacterial agent. Shrinking agents may include de-wormers. Examples of de-wormers include one or more of mebendazole, fenbendazole albendazole (ABZ), flubendazole (FUBZ), oxibendazole (OBZ), or Panacur™ (a horse de-wormer that can also be used on humans). Some of these de-wormers may also induce an anti-cancer response. See https://www.cancertreatmentsresearch.com/fenbendazole/. Other examples of anti-cancer agents include anthracyclines, such as berubicin which can cross the blood brain barrier. Ferumoxytol can provide a biomarker of inflammatory cells and may provide clinical guidance in differentiating true tumor progression from pseudoprogression.

A lubricant may include a cryophilic lubricant, such as liquid nitrogen or supercooled nitrogen gas, and saline. Such lubricants adhere to and create a thin film upon the tumor that may make it easier to remove. For example, liquid nitrogen can be applied through the chemical feed path 134 as a microspray that can create a cryofrost, upon the targeted tumor 122. Moreover, this cryofrost is visible as a white surface frost on the tumor tissue, which helps to visually differentiate the tumor 122 from the healthy tissue 124 but also acts to destroy the tumor 122. One will appreciate that a flash chill tip (as later described) touches directly to propagate temperature across all tissues that are contiguous to the contact location; however, a microspray can spread the frost further externally than actual contact via a fluid or other interstitial space.

Examples of anti-bacterial agents include taurolidine and taurultam, which may also have anti-cancer effects, and may be utilized to help prevent infection and to address any tumor cells that may be inadvertently left behind.

Biological agents may include proteins, antibodies, or engineered viruses. These biological agents and chemicals 142 may be delivered individually, sequentially, or simultaneously, depending on their compatibility and the timing of when they are most effectively applied. Monoclonal antibodies may act as anti-cancer agents. For example, rituximab has excellent efficacy in preclinical models of CNS lymphoma.

The chemical feed path 134 may also serve as a vacuum pathway and serve as a suction tool, or a separate suction pathway may be employed. One or more suction tools may be employed to remove blood from an area during surgery or to assist the grasping tool dislodge a tumor 122 (as later described).

The microsurgical probe 120 may also include one or more resonator motors 150, such as an adaptive resonator or an adaptively unbalanced resonator. Examples of resonator motors 150 include piezoelectric actuators that can operate down to the size level of nanometers. Piezoelectric actuators would be well suited for applications associated with a microsurgical probe 120. Piezoelectric materials can cause mechanical movement in response to electrical stimulation, and they can create electrical charge when mechanically stressed. Moreover, a piezoelectric material can also be used to measure changes in pressure, acceleration, temperature, strain, or force by converting them to an electrical charge. Piezoelectric actuators can change dimensions when an electric potential is applied, and they can provide a variety of types of motion, including lateral motion or bending motion. They are commercially available in stacks of thin layers that extend when voltage is applied to them.

The motors 150 operate based on a range of drive types. One drive technique uses piezoelectric ceramics to push a stator. These piezoelectric motors 150 are basically stepping motors and are also known as "inchworm motors." Another type of drive force for a suggested embodiment of probe 120, employs piezoelectric motors 150 that produce surface acoustic waves to generate a linear or rotational motion. A version of a direct drive mechanism for these nanometer-sized motors, include piezoelectric elements bonded orthogonally to a nut, such as for a squiggle motor. The ultrasonic vibrations from these motors 150 can rotate a central lead screw.

In particular, piezoelectric resonator motors 150 may produce forces up to 1000 Newtons (N), may have sub-nanometer (nm) resolution, and may be are self-locking. Some piezoelectric resonator motors 150 operate by producing ultrasound at 1 um/sec to 500 mm/sec, with fast step and settle mechanisms. These types of piezoelectric resonator motors 150 can be applied for linear and/or rotary motion, or the ultrasound vibrations themselves may be useful for some applications. For example, the resonator motor 150 may be employed to loosen tumor tissue 122 from healthy tissue by vibration. Some piezoelectric resonator motors 150 have 20 nm resolution with position encoders. Some piezoelectric resonator motors 150 may act as mini-rods with nanometer resolution, sensor options, and application of 10 N force. One or more of these resonator motors 150 may be positioned in proximity to the probe tip 128.

The resonator motor 150, whether piezoelectric or not, may be employed to activate or actuate one or more probe accessory tools 160, such as a grasping tool (such as depicted in FIG. 1A) a piercing tool 360 (such as depicted in FIG. 3A), a scraping tool, and injection tool. A grasping tool may be configured as a tweezer, or pliers, and/or with forked or hooked teeth to allow for firmly snagging a targeted tumor 122. They may be spring based and retractable. These capabilities may be provided by piezoelectric actuators as previously discussed or by other types of micromotors. Piezoelectric probe accessory tools 160 may be able to bend, grab, or ratchet. A forceps-like actuated grasping tool is described in U.S. Pat. No. 6,322,578 of Houle et al. This forceps-like device could be miniaturized and modified by employing small enough piezoelectric actuators to function as a probe accessory tool 160. The probe accessory tools 160 may loosen tumor tissue 122 by abrasion, grasping, or peeling, for example.

Some embodiments of probe accessory tools 160 may provide temperature, light, radiation, laser beams, vibrations, and/or sound instead of, or in addition to, operations based on movement. These capabilities may be provided by piezoelectric actuators as previously discussed or by other types of microdevices associated with the specific function.

These probe accessory tools 160 may be housed in micro-receptables at or near the probe tip 128. The receptacles may act to retain the probe accessory tools 160 when they are not being employed so that the probe accessory tools 160 are not damaged, or so that they do not damage tissue, when they are not being used. The microsurgical probe 120 can be configured to have a universal connector suited to accommodate different probe accessory tools 160. This type of design would permit a generic embodiment of a microsurgical probe 120 to be manufactured and then subsequently outfitted with the appropriate tool attachment so that it would be configured for particular applications, such as tumor removal or sperm "injection." Thus, the attachments may be exchangeable. Or, these attachments may be attached and removed through accessory adaptors fitted for each tool. These adaptors or universal connector would enable probe accessory tools 160 to be attached by sliding on, twisting, or locking in place. The adaptors or universal connector may also feature press fit or magnetic fittings to accommodate micro- and/or nano-size range options or alternatives.

Some embodiments for manipulating the probe tools 120 or 360 incorporate recent advances in robotic technology. See https://www.ncbi.nlm.nih.gov/pubmed/17406589 and https://www.ncbi.nlm.nih.gov/pubmed/10099992). Piezoelectrically driven probes and grasping, injecting, and piercing tools can also be robotically controlled. Some examples include protocols that involve multiple applications, including nuclear transfer cloning, spermatid injection, blastocyst injection, and transgenesis. In some of these protocols, a piezoelectric micromotor effects crystal deformation in response to an externally applied voltage. This results in propelling a microinjection needle tip forward in a precise and rapid movement. Piezoactuated micromanipulation may enhance the penetration of membranes and matrices, and mouse ICSI is a major application. In piezoelectrically enhanced ICSI, for humans, the needle used may have a flat tip instead of a sharp tip. However, deformation of the oocyte (the haploid egg or ovum), during insertion of the needle may be restrained by vibration of the piezoelectric actuator. And, the egg coat (or oolemma, zona pellucida, vitelline membrane) may be punctured by a piezoelectric pulse so the spermatozoon may be injected.

The probe tip 128 may include a flash chill tip that may be employed to flash freeze tissue such as a target tumor 122 to make it easier to remove or that may be employed to chill healthy tissue to minimize damage by inflammation. In one embodiment a flash chill tip, employs concepts similar to a trans-corneal freezing machine that utilizes a freezing console and nitrous oxide as a cryogen to cool a series of different cryoprobe tip designs. The tips may be made of silver to provide high thermal conductivity. This process is described at https://www.ncbi.nlm.nih.gov/pmc/articles/PMC5448072/.

One or more sensors 152 may be attached to the microsurgical probe 120 or they be employed separately to inform, guide, and/or instruct the microsurgical probe 120 or its probe accessory tools 160. Common sensors 152 may include image sensors such as endoscope cameras, sound sensors, or temperature sensors. Other variations of sensors may include audio sensors that can detect heartbeat or other vibrations, or chemical sensors that can measure pH, viscosity, and pressure. These sensors 152 may be attached via adaptors on the microsurgical probe 120, by insertion, screwing on, twisting on, winding on, locking, press fitting or magnetically.

A sound sensor may convey sound data to a software processing system, which may convert the sound data into a visual graphic or incorporate the sound data with other data to facilitate operation of a controller. The microsurgical probe 120, its probe accessory tools 160, its resonator motor 150, its probe tip 128, its optical fiber emissions, its chemical deliveries, and its associated sensors 152 may be controlled by conventional means. For example, the microsurgical probe 120, its probe accessory tools 160, its resonator motor 150, its probe tip 128, its optical fiber emissions, its chemical deliveries, and its associated sensors 152 may be controlled by robotic actuators. These probe accessory tools 160 and associated sensors 152 may be controlled by as software processing system through piezoelectric motorized robotic actuators, for example, as previously discussed.

The sensors 152 may relay information to a software processing system that may include an artificial intelligence (AI) system to assist with operations of one or more of the elements of the microsurgical probe 120 (such as through one or more controllers), particularly with one of its probe accessory tools 160. The software processing system may utilize machine learning to improve performance of the elements of the microsurgical probe 120. For example, the AI system may identify tumor conditions and forecast preferred timing for a procedure, such as identifying when tumor periphery is adequately lubricated and when resonance has adequately loosened tumor tissue before grasping or manipulation is performed with the probe accessory tools 160. In particular, if a tumor periphery is adequately lubricated, relative slip can be detected visually. If the threshold of slip exceeds a specified threshold, then the tumor periphery would be identified as a lubricated target, in contrast to unlubricated areas of tissue.

In another example, the AI system may identify regions around the tumors that are bleeding and determine the amount and nature of such bleeding. Visual, chemical, and/or physical data sensor information may be conveyed to the AI system for analysis. An extraction of a cancer tumor may cause bleeding for a variety of reasons. Extraction of a tumor may cause bleeding due to its own fragile blood vessels. Tumors often enlarge and invade surrounding tissues. For example, a tumor may grow into a nearby blood vessel in healthy tissue. The likelihood of a cancer tumor extraction causing bleeding upon its removal may be dependent on its location. For example, extraction of a cancerous tumor located along the digestive or urinary tract, or in the heart, or in the lungs will cause external and internal bleeding. In some embodiments, the microsurgical probe 120 can be adapted for cauterization of bleeding sites. After the AI determines the location, amount, and nature of the bleeding site(s), then the AI system may employ robotic piezoelectric mechanized guidance of the optical fiber 130 to the site(s) that are bleeding and need repair. In one example of the cauterization process, the optical fiber 130 of microsurgical probe 120 can emit a laser beam at an appropriate wavelength, pulse length, and repetition rate to cauterize the exposed healthy tissue to stop the bleeding. In another example of the cauterization process, the AI system can actuate the piezoelectric mechanism to guide the chemical feed path 134 to the bleeding sites and release the appropriate chemical, such as a coagulant, in a suitable volume and concentration to stop the bleeding or repair the damage.

In another example, the AI system may identify when the outer surface of the ovum 366 (FIG. 3A) is adequately lubricated. In particular, the AI system may employ visual, chemical or physical sensors to detect a certain minimum thickness around the membrane of the ovum. When an acceptable threshold is reached, the AI system may activate the piezo-mechanism 150 can be actuated to cause the piercing tool 360 to pierce the ovum 366 in preparation for injection of sperm 364 via the coaxing actuator 362. In another embodiment for preparing the ovum 366 for injection of sperm 364, the piercing tool 360 may be exchanged for an aspiration or vacuum tool; or the feed path 140 or the microsurgical probe 120, itself, may be configured for aspiration or vacuum. Such a modification of ICSI process may improve outcome. The aspiration of the ovum or a portion of it into the aspiration channel may introduce a micro-rupture in the ovum 366, prior to injection of the sperm 364. Oolemma rupture inside the intracytoplasmic sperm injection needle may significantly improves the fertilization rate and reduce oocyte damage.

In another example, the AI system may (perhaps through an injection needle controller) control the location and angle of injection, the rate and alternation of needle approach and retreat, the rate and modes of resonant vibration of the needle, and/or the rate of sperm injection. These can be modified in association with learned data.

In another example, the AI system may identify multiple candidate injection sites that can be test pressed and vibrated before an actual injection is attempted. Moreover, the AI system may identify when a trial press to a location along the outer surface of the ovum may be least vulnerable to bursting. For example, the AI system may analyze visual, chemical, and/or needle force feedback (such as measured by spring force and compression) data and compare such data to database references to determine the degree of risk of ovum membrane bursting. Additionally, the AI system may control auxiliary tools 368 (FIG. 3A), such as holding devices, to rotate, loosen, or compress the ovum 366 as test sites on it are evaluated, as later described.

The AI system may employ one or more of artificial intelligence type computers and digital data processing systems and corresponding data processing methods and products for emulation of intelligence (i.e., knowledge-based systems, reasoning systems, and knowledge acquisition systems). These systems include but are not limited to systems for reasoning with uncertainty (e.g., fuzzy logic systems), adaptive systems, machine learning systems, and artificial neural networks (as further delineated in CPC Classification System, section 706—Data Processing—Artificial Intelligence). In particular, the AI system may employ one or more of a neural network, a probabilistic technique such as Bayes or Markov algorithm, a kernel method (like SVM, decision trees/random forest, Gaussians, PCA, can-cor . . . ). The AI system may also employ one or more of a reinforcement learning system that can have nothing to do with artificial neural networks, artificial reasoning a.k.a. "good old-fashioned AI," many path-planning and intelligent control-systems methods that correspond to "classical AI" (not the same as GOFAI), alife (swarms, cellular automata . . . ), and agents and chaos systems. The AI system may additionally include any algorithm or group of algorithms that optimize a value function (reinforcement learning and linear dynamic programming).

An embodiment of an AI system-powered ultrasound-guided tool, such as for the manipulation of the microsurgical probe 120, such as shown in FIG. 1A-1C or 3A, includes an automated target identification system. These systems use a machine-learning algorithm to identify organic landmarks during an ultrasound. This technology is already in use in medical applications. Examples include those used for insertion of needles for spinal anesthesia. In this example, an anesthesiologist is alerted in real time when the system identifies the right location and right angle for insertion. Some of these examples are described at https://www.beckersspine.com/spine/item/47438-study-ai-powered-ultrasound-guided-system-boosts-spinal-anesthesia-success.html. Other examples of the application of the AI system, employ audio sensors, such as those applied for the detection and evaluation of a fetal heartbeat. Such applications are provided here for illustration. See https://ars.els-cdn.com/content/image/1-s2.0-S1361841517300117-fx1_lrg.jpg.

Other embodiments of AI systems employed by the microsurgical probe 120, such as shown in FIG. 1A-1C or 3A, may similarly use laser, video, and sonographic imaging to guide the microsurgical probe 120 or its probe accessory tools 160 and 360. Some embodiments would employ steps similar to those used in the above examples. These steps may include neural network training and algorithms to cluster responses into groups for different approaches, while detecting imaging data or resonance frequency. These processes would then be merged into the network, and results would signal the tools instructions of where, when, and how to act. Medical technology that employs fluorescence-guided surgery (FGS) can be adapted for guiding the microsurgical probe 120 or its probe accessory tools 160 and 360. In FGS, tumor location and margins can be defined during the operation. Intraoperative visual imaging of tumors may allow more complete resections and avoid unnecessary damage to normal tissue. A number of new FGS imaging probes have recently been developed, complementing a small but useful number of existing probes. A review article that details these types of probes may be found at https://www.frontiersin.org/articles/10.3389/fonc.2017.00314/full.

Figure 1B:
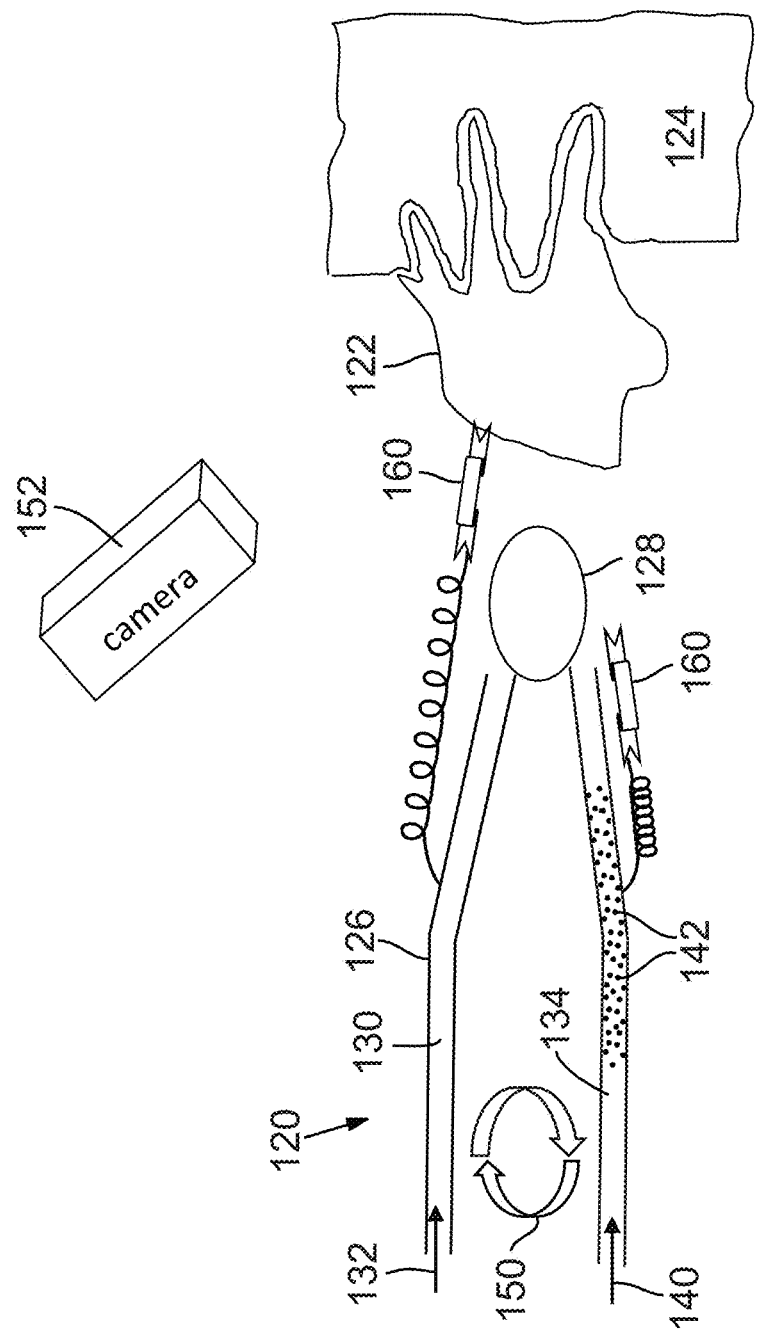
FIG. 1B illustrates an embodiment of a microsurgical probe with a grasping tool extended in the process of grabbing the tumor.
Figure 1C:
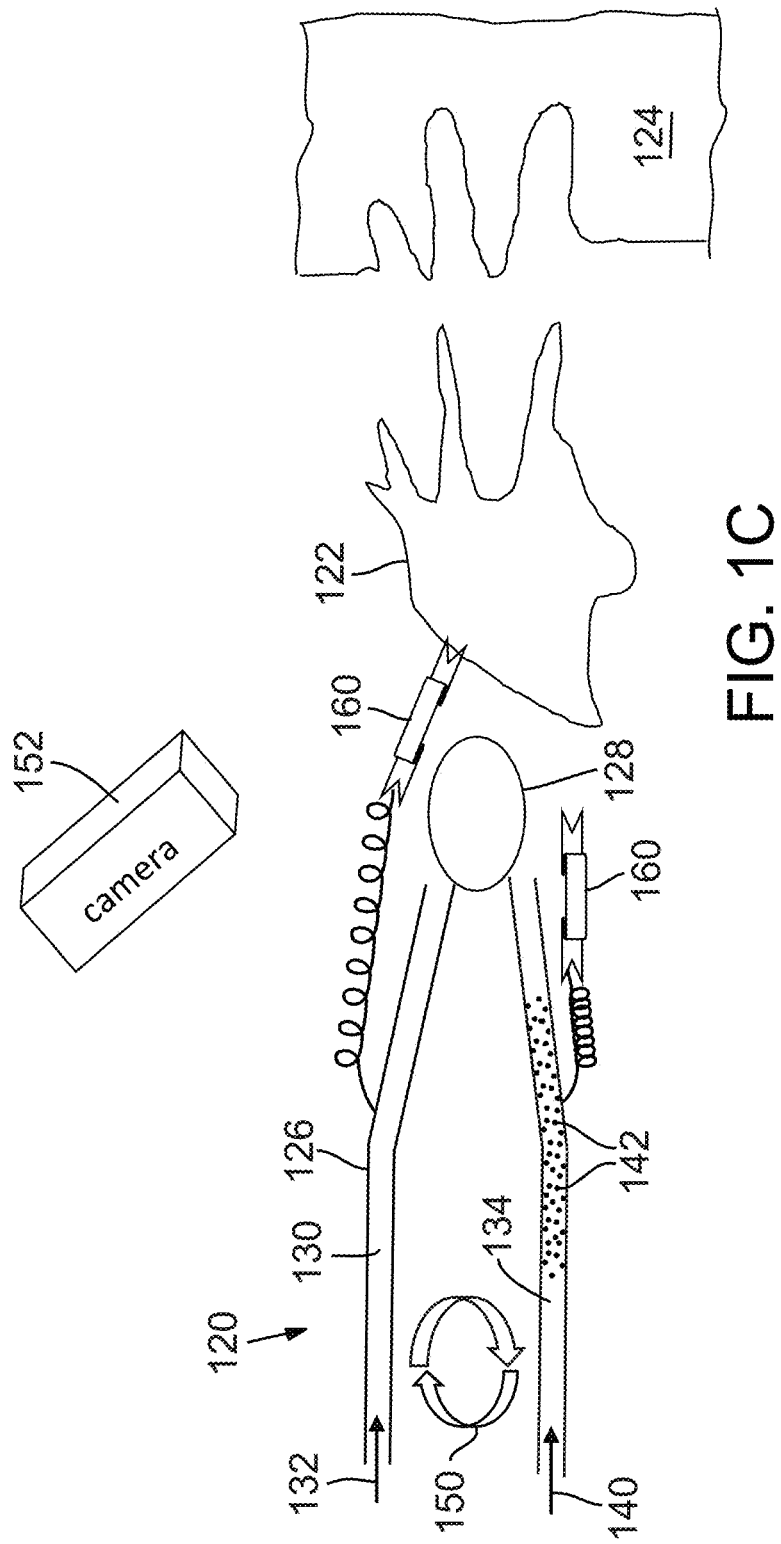
FIG. 1C illustrates an embodiment of a microsurgical probe with the grasping tool holding the tumor successfully extracted from the healthy tissue.
Figure 2:
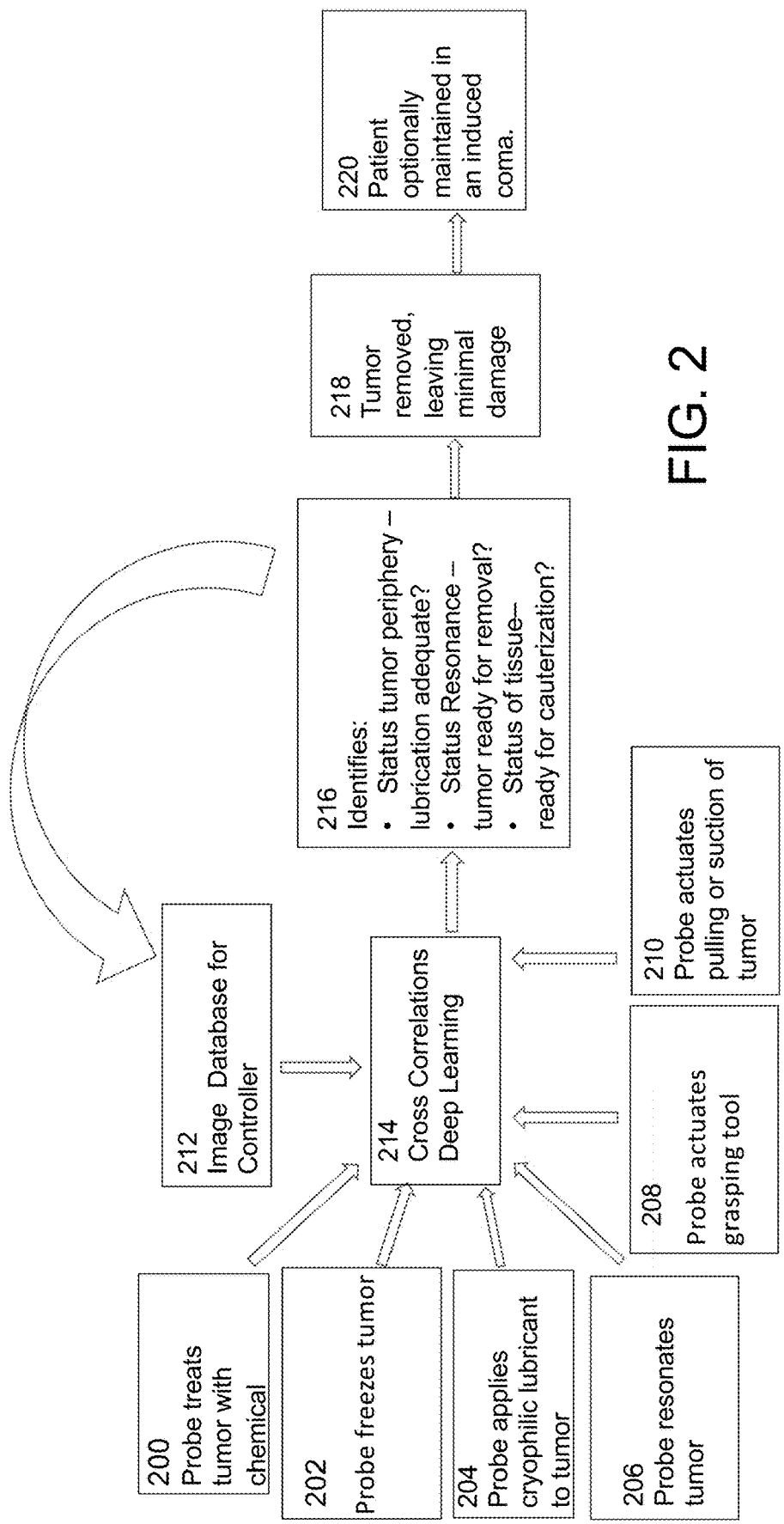
FIG. 2 illustrates process steps that employ a microsurgical probe to remove tumor tissue that may be interwoven with healthy tissue.

FIG. 1B illustrates an embodiment of the microsurgical probe 120 with a probe accessory tool 160 in the form of a grasping tool that is extended in the process of grabbing the tumor 122. FIG. 1C illustrates an embodiment of the microsurgical probe 120 with the grasping tool holding the tumor 122 successfully extracted from the healthy tissue 124. FIG. 2 illustrates an example of process steps that employ the microsurgical probe 120 to remove tissue of a tumor 122 that may be interwoven with healthy tissue 124.

Prior to a tumor removal process, patient data including vital signs and other information including CT or other scans of the patient can be loaded into the software processing system. The AI system (such as represented by a process step 214 in FIG. 2) may compare the patient data and scans to those used in previously procedures for other patients. The processing software system may provide recommendations for presurgical procedures such as pre-medicating the patient, adjusting patient temperature, determining the spatial orientation of the patient for the procedure, and determining probe contact point and its trajectory.

For example, the software processing system may recommend that some medications be ingested or provided intravenously. Examples of chemicals for pro-operative ingestion may include a de-wormer or a tumor shrinking agent or anti-bacterial or anti-cancer agents. If the tumor is in the brain and the chemical is to be ingested, then the chemical should be capable of crossing the blood-brain barrier.

In some circumstances, possibly determined by the AI system (such as represented by the process step 214), the entire patient can be chilled and placed into an induced coma to reduce damage from the swelling of healthy tissue 124 that is interwoven with the tumor 122.

With guidance from the software processing system, the micro-sensors 152 can be suitably positioned with respect to the tumor 122. This task may be accomplished by positioning the microsurgical probe 120 in a suitable location, if the sensors 152 are attached to the microsurgical probe 120. If the sensors 152 are separate, they may be positioned before the microsurgical probe 120 is guided into position by appropriate controllers as instructed by the software processing system in cooperation with image database 212 (FIG. 2), which may be responsive to data provided by the pre-positioned sensors 152 as well as pre-operative patient scans (such as represented by the process step 214).

With reference to FIGS. 1A-1C and 2, the microsurgical probe 120 can be positioned in an optimal location for multiple probe operations or in sequential optimal locations for sequential probe operations with respect to the specific tumor 122 to be extricated. In one example, the software processing system determines an initial prospective order of probe operations and positions the microsurgical probe 120 accordingly with data from the image database 212 and with data from previous procedures on other patients (such as represented by the process step 214) and conveys the information or instructions to the probe movement controllers. One will appreciate, however, that the software processing system (or the operator, such as a surgeon) may determine that the order of probe operations should be changed based on sensor information or observed tissue responses (such as represented by the process step 214).

In an example tumor-removal procedure, the site of tumor removal (the tumor 122 and closely surrounded healthy tissue) can be chilled to reduce damage from prospective swelling of the healthy tissue 124 that is interwoven with the tumor 122. This chilling of the entire site can be accomplished by chilling the entire patient or by controlled use of a temperature-reducing chemical or other temperature-reducing means available to the microsurgical probe 120.

In a process step 200, a de-wormer chemical 142 is applied along the chemical feed path 134 to the tumor 122. The de-wormer chemical 142 may shrink the tumor 122 and cause it to become denser and/or more malleable so that it can be removed more easily without breaking apart. The software processing system may utilize data from previous procedures to inform (such as represented by the process step 214) the concentration, volume, application rate, and direction of the de-wormer chemical 142 as it exits the chemical feed path 134.

In a process step 202, the microsurgical probe 120 freezes the tumor 122. Freezing the tumor 122 may be accomplished by use of a flash chill probe tip 128 or by application of a solid powder or a short burst of liquid or supercooled gaseous nitrogen through the chemical feed path 134 (or through a secondary chemical feed path 134) to the tumor 122. The solid powder may provide an endothermic reaction upon touching the surface of the tumor tissue causing the tumor 122 to cool. The software processing system may utilize data from previous procedures to inform (such as represented by the process step 214) the concentration, volume, application rate, and direction of the nitrogen as it exits the chemical feed path 134. Chilling the area around the site of tumor removal may help minimize damage by inflammation of the remaining healthy tissue 124.

In a process step 204, the microsurgical probe 120 may apply another chemical 142, such as a cryophilic lubricant that can selectively attach to the colder surface of the tumor tissue and coat it with a thin layer of the lubricant. Freezing the tumor 122 and/or applying the cryophilic lubricant my create a cryofrost upon the tumor tissue that is visible as a white surface frost on the tumor 122. This cryofrost may not only help differentiate the tumor 122 apart from the healthy tissue 122, but the freezing or cryofrost may act to destroy the tumor tissue, especially around the periphery of the tumor 122. Alternatively, a tumor-selective or tissue-selective dye may be propagated through the chemical feed path 134 to help the sensors differentiate the tumor 122 from the healthy tissue 124.

In a process step 216, the software processing system as represented by the process step 214 may utilize data from the image database 212 and current data provided by the sensors 152 to determine whether the conditions are appropriate for proceeding with the next procedural step. For example, the software processing system may determine whether adequate lubrication has been applied to the tumor periphery. If not, the software processing system may implement feedback control responsive to data by the sensors 152, data from the image database 212, and the cross correlations deep learning 214 to achieve satisfactory status.

In a process step 206, the resonator motor 150 of the microsurgical probe 120 may be activated by an appropriate controller in response to satisfactory conditions being determined in the process step 216. The resonator motor 150 may shake the tumor 122 and loosen it from the healthy tissue 124. The process step 206 may be controlled by the software processing system such as represented by the process step 214 that may establish the resonator frequencies, intensity, and duration, and the software processing system may modify or these variables or repeat resonator motor treatment as feedback control responsive to data by the sensors 152, data from the image database 212, and the cross correlations deep learning 214 to achieve satisfactory status, such as whether the tumor 122 is ready for removal.

Alternatively or additionally, the microsurgical probe 120 can be configured to emit a sound frequency that resonates the tumor 122 to it. The sound may be made by the resonator 150 and emitted from electrostatic or piezo-electric speakers. The sounds may be in the human audible range, ultrasonic, or in the radio-wave spectrum. Resonance mode and sound pressure may be produced by circular diaphragms of electrostatic and piezoelectric speakers. Examples of how these sounds are produced from electrostatic or piezoelectric speakers are described in https://www.sciencedirect.com/science/article/abs/pii/S0003682X17302712, https://www.americanpiezo.com/standard-products/buzzers.html, and https://www.edn.com/piezoelectric-driver-finds-buzzers-resonant-frequency/.

In a process step not shown, the software processing system may identify areas where the tumor tissue is sticking to the healthy tissue even after repeating freezing and lubricating steps. The software processing system may guide the optical fiber 130 of the microsurgical probe 120 into appropriate position(s) and provide laser emissions suitable for ablating or severing the connections between the tumor 122 and the healthy tissue 124. Data from sensors 152 can be used to determine whether such operations are successful or whether further laser treatment is recommended in the process step 216.

In a process step 208, one or more of the probe accessory tools 160 of the microsurgical probe 120 may be activated to grasp the tumor 122. In response to data by the sensors 152, data from the image database 212, and the cross correlations deep learning 214, the software processing system may determine whether the tumor 122 is adequately grasped by the grasping tool or whether a better grasp should be established.

In a process step 210, the grasping tool 160 may retracted and suction may be applied through the chemical feed path 134 (or a secondary channel) as directed by the software processing system, which may also determine the appropriate amount of retraction force to provide and the amount of vacuum to provide and may coordinate the cooperation between the grasping tool 160 and the vacuum.

Some embodiments of the grasping tool 160 may be adapted for vacuum-assisted extraction of tumors from healthy tissue. For example, technology that is already used in the medical field for ultra-sound guided, vacuum-assisted removal of breast lesions may be implemented with the microsurgical probe 120. (See https://www.ncbi.nlm.nih.gov/pmc/articles/PMC4248624/ for more details.)

Some embodiments of the grasping tool 160 may be utilized in conjunction with surgical treatments like neuroendoport surgery that incorporate suction. These methods provide surgeons with minimally invasive access to tumors 122 through a dime-size channel. The microsurgical probe 120 and/or its probe accessory tools 160 and 360 may be is inserted through the neuroendoport device, providing light and video images that guide the surgeon. Pressure from the tumor mass and suction from the probe 120 may deliver the tumor 122 into the microsurgical probe 120 or the neuroendoport. In this description, suction is used to remove the tumor 122. More information on this type of surgery may be found at https://www.upmc.com/services/neurosurgery/brain-tumor-removal-using-neuroendoport-transcript.

The software processing system may establish parameters associated with tumor extraction (or ICSI). Some of these parameters may include speed, angle, vibration frequency, resonant modes, tumor grasp area, tumor grasp pressure, etc. that may be involved in tumor removal. Moreover, the software processing system may monitor to perceive damage to tissues surrounding the tumor material before and after it is removed. If a damage threshold is perceived to be crossed, the software processing system may change the parameters to mitigate the damage.

In the process step 216, the software processing system can utilize the cross correlation deep learning process 214 to establish in conjunction with sensor data and historical data whether the tumor 122 has been completely removed or whether any portions of it are still attached to healthy tissue 124. The software processing system can direct the components of the microsurgical probe 120 to repeat any of the procedural steps until the software processing system determines that the tumor 122 is completely removed or that no further removal processes should be attempted.

Additionally, the software processing system can utilize the cross correlation deep learning process 214 to establish in conjunction with sensor data and historical data whether there are any tissue tears around the tumor removal site, determine the size of these tears, and detect whether there is any bleeding around the tumor removal site. Large tissue tears at a tumor removal site can result in substantial blood loss in a short amount of time. Blood loss may be a primary risk factor for tumor removal, especially in the brain where bleeding can cause very serious issues.

The AI system may also be used to detect symptoms of intracerebral hemorrhage such as sudden weakness, tingling, or paralysis in the face, arm, or leg, especially if they occur only unilaterally on one side of the body. Other symptoms may include sudden onset of severe headache, trouble swallowing, trouble with vision in one or both eyes loss of balance and coordination, dizziness, and trouble with language skills (reading, writing, speaking, understanding). Other symptoms of intracerebral hemorrhage may include nausea, vomiting, apathy, sleepiness, lethargy, loss of consciousness, confusion, and delirium.

Other risks associated with removing a tumor 122 that is interwoven with healthy tissue 124, or is adjacent to healthy tissue 124, is damage to the healthy tissue 124, itself, during and after tumor extraction. This factor may also be very serious in the brain where damaging tissue may cause impaired brain function. Moreover, damaged may lead to infection or swelling. Inflammation can initiate a chain reaction that can lead to blockages in circulation and compromise the cellular immune response, limiting access for antibodies and t-cells.

The chemical feed path 134 (or an alternative channel) on the microsurgical probe 120 may serve as a vacuum channel that can be used to remove blood from the tumor removal site. Blood removal may help the sensors isolate the locations where bleeding is occurring.

In accordance with the process step 216, the software processing system may determine the appropriate probe-related procedure to apply in response to identified tissue damage or bleeding. For example, the software processing system may cause the microsurgical probe to dispense a medical glue or adhesive through the chemical feed path 134 (or through an alternative channel) to mend, seal, glue tears to prevent additional bleeding from the tumor removal site. One will appreciate that delivery of a glue or adhesive may be a one-time and final use of any given chemical feed path 134.

Alternatively, the software processing system may cause the microsurgical probe 120 to propagate laser light along the optical fiber 130 to cauterize the cite of bleeding. One will appreciate that the microsurgical probe 120 may be configured to provide flash heating at the tumor-removal site, either by electrical charge, a heating element, or by adding a chemical 142 that produces an exothermic reaction. One may also appreciate that flash heating may be used for tumor destruction or to assist with tumor removal.

Alternatively or additionally, the microsurgical probe 120 may be configured to apply micro-sealing adhesive. In one embodiment, a single use a plunger assembly may be attached to the microsurgical probe 120 as a probe accessory tool 160, or the sealant may be dispersed through the chemical feed path 134. An example of a sealant that can be used for this embodiment includes fibrin, which has for example been used as an adhesive in ocular microsurgery of the anterior segment of the eye. The AI system may analyze the database to determine the best method of suturing, adhesive application, or cauterization a bleeding site for embodiments based on past experience with the particular type of sealants and sizes and shapes of the wound.

In a process step not shown, the microsurgical probe 120 may dispense an anti-bacterial agent to reduce the risk of infection and/or an anti-cancer agent to capture or destroy any cancer cells that may have been left behind after a tumor extraction process.

In a process step 218, the software processing system can utilize the cross correlation deep learning process 214 to establish, in conjunction with sensor data and historical data, whether all of the tumor tissue 122 has been successfully removed and that any damaged tissues have been addressed and any bleeding has been stopped. In a process step 220, the patient may be kept in an induced coma and optionally chilled to mitigate post-surgical inflammation and damage. One will appreciate that any of these process steps may be omitted or the order of the process steps may be changed.

Another example of a microsurgical probe 120 can be employed for intracytoplasmic sperm injection (ICSI) and may be particularly useful for implementing ICSI in older mammalian eggs that may have a tendency to be relatively inflexible and burst during conventional ICSI procedures. In particular, FIG. 3A illustrates an embodiment of a microsurgical probe 120 suitable for fertilizing an ovum 366 that is susceptible to bursting, such as a human or horse ovum 366 that is older than 30 years or older than 40 years. For convenience, components in FIG. 3A that are similar to components presented for FIG. 1A have been labeled with the same reference numerals. Furthermore, all of the capabilities previously discussed with respect to the microsurgical probe 120 of FIG. 1A apply to the microsurgical probe 120 of FIG. 3A. However, FIG. 3A shows piercing tools 360 as the embodiment of the probe accessory tool 160 and additionally shows a sperm-coaxing actuator 362. The piercing tools 360 are configured to penetrate the outer surface of the ovum 366 without bursting it. The coil portion or springs associated with the probe accessory tool 360 can be piezo-electrically actuated as previously described.

Figure 3B:
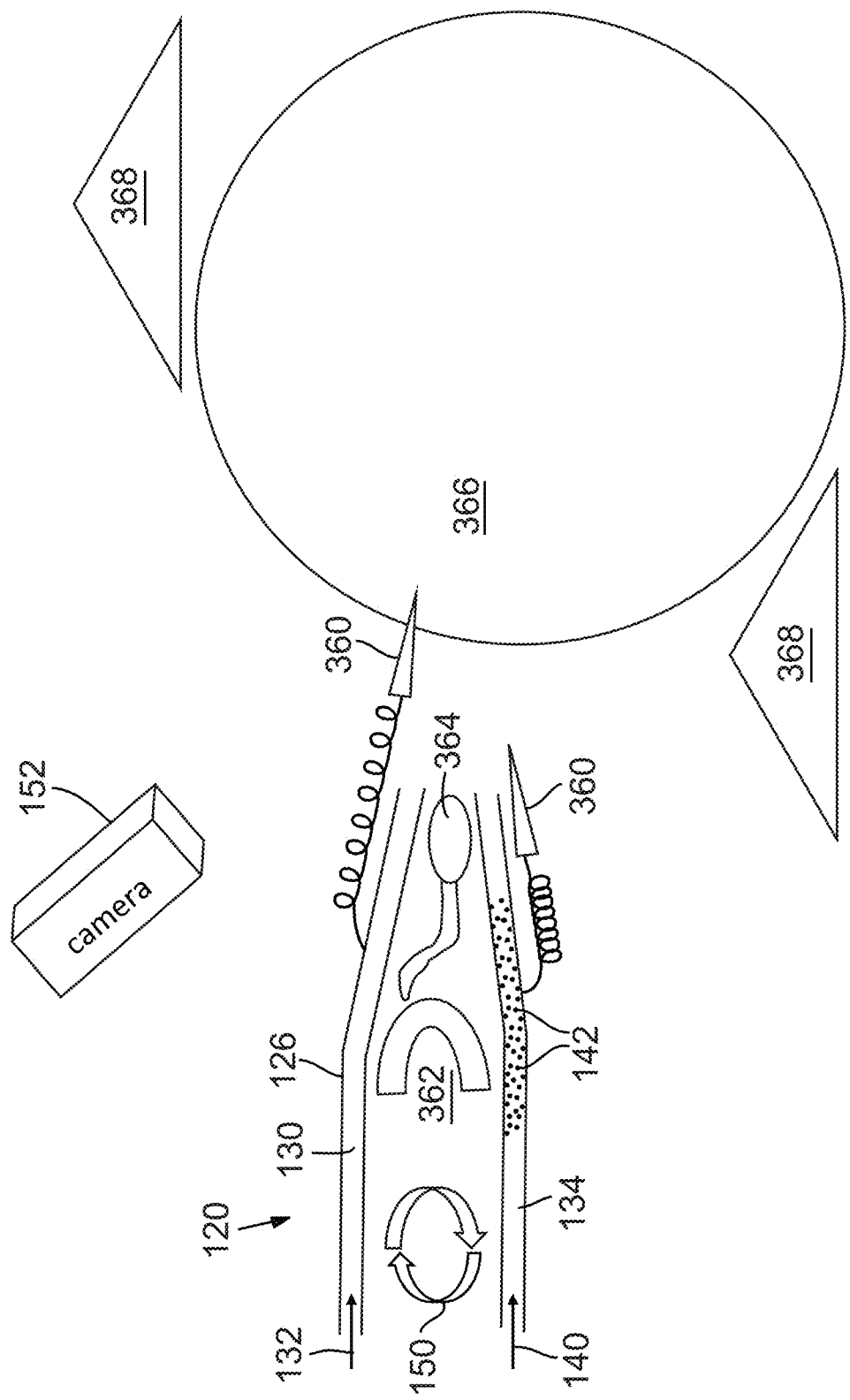
FIG. 3B illustrates the use of a piercing tool of a microsurgical probe for facilitating the entry of a sperm cell to fertilize an ovum that is susceptible to bursting.
Figure 3C:
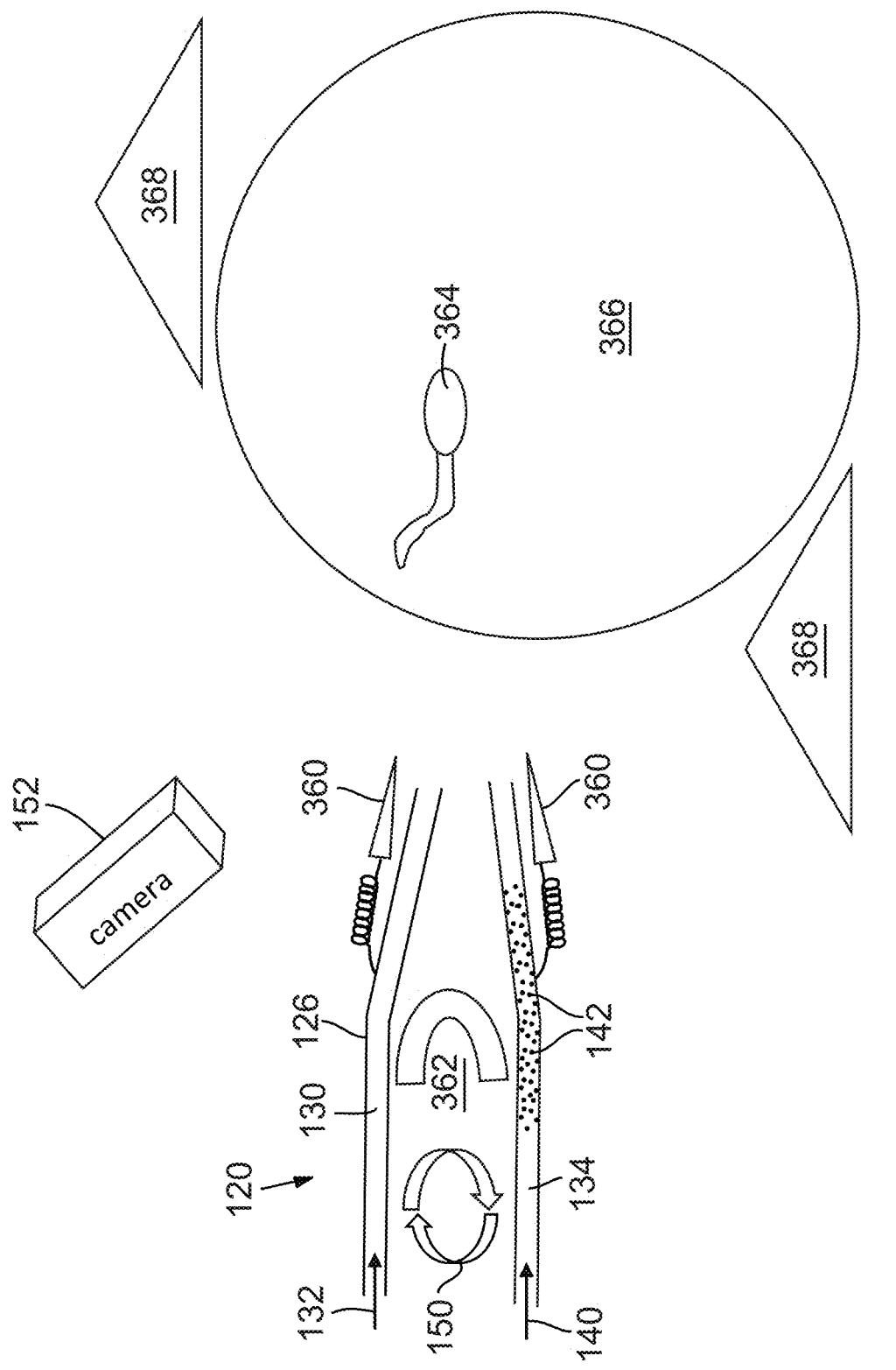
FIG. 3C illustrates the successful entry of a sperm cell into the susceptible ovum after use of the piercing tool of the microsurgical probe.
Figure 4:
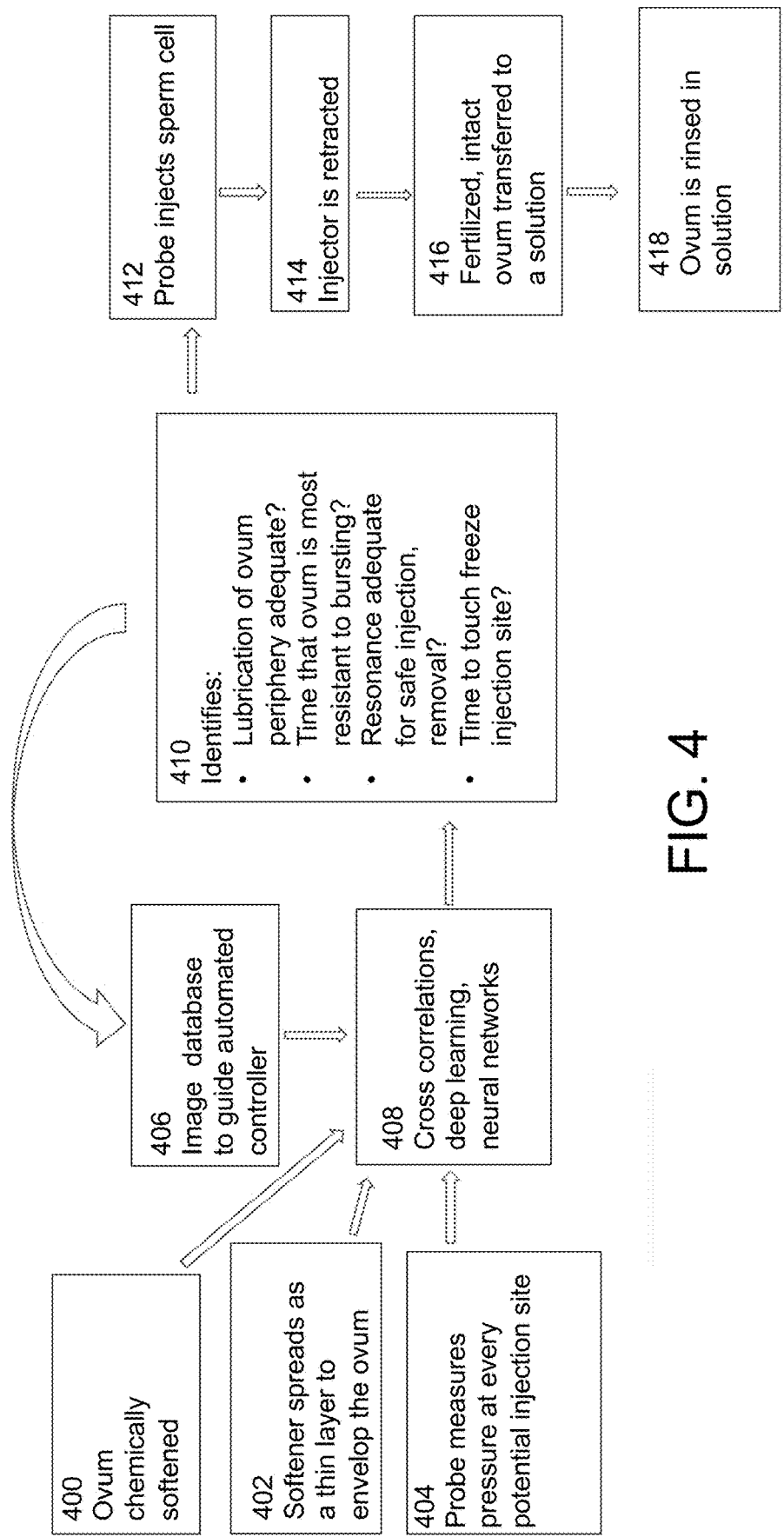
FIG. 4 illustrates process steps that employ a microsurgical probe to fertilize an inflexible ovum.

FIG. 3B illustrates the use of one of the piercing tools 360 of the microsurgical probe 120 to create an opening to facilitate entry of a sperm cell 364 to fertilize the ovum 366, which may be susceptible to bursting. FIG. 3C illustrates the successful entry of the sperm cell 364 into the ovum 366 after retraction of the piercing tool 360 of the microsurgical probe 120. FIG. 4 illustrates process steps that employ the microsurgical probe 120 to facilitate fertilization of an older ovum 366. An older ovum 366 may be a mammalian ovum, such a human ovum or a horse ovum that is passed an ideal age for natural and successful insemination. One will appreciate that the probe accessory tools 360 may be employed to test the membrane of the ovum 366 or may be employed to help pierce the membrane if the whole tip of the microsurgical probe 120 is intended to enter into the ovum 366. If the tip of the microsurgical probe 120 is larger and the membrane is partly sucked into the end of the tip, then the probe accessory tools 360 may be employed to stabilize the rest of the ovum 366.

The ovum 366 may be held by a pipette that applies gentle suction to stabilize orientation of the ovum 366 as may done for conventional ICSI procedures. Alternatively, a second microsurgical probe (not shown), which may be another embodiment of the microsurgical probes 120 described herein, may be employed to maintain the ovum with enhanced positional control with gentle suction provided through one or more of its chemical feed paths (or alternative channels). Such a second microsurgical probe 120 may have a hollow needle probe structure configured to partly surround the ovum 366, or such probe 120 may employ a flash chill tip 128. Additionally or alternatively, the ovum 366 may be manipulated, such as statically held, rotated, loosened, or compressed, by auxiliary tools 368 as test sites on the ovum 366 are evaluated by the probe accessory tools 360 and the AI system.

The ovum 366 may be optionally pretreated with a chemical before being suitably positioned or a pretreatment chemical may be delivered through a chemical feed path 140 of a probe 120 used to hold the ovum 366. Embodiments of ova-softening or pre-conditioning chemicals are FSH, hCG, and TCM-199 buffered with bicarbonate or HEPES, supplemented with various sera, gonadotrophins and steroids. These chemicals may condition the oocyte to allow penetration without resistance. These chemicals may be prepared and dispensed by the microsurgical probe 120 in carefully measured amounts to avoid rupturing the ovum. Even calcium administered very carefully can properly condition the ovum 366.

In addition, the diverse range of physiochemical properties of water can be applied towards ovum preparation. For example, intracellular water (also called vicinal water) is organized differently than bulk water. Vicinal water is affected by the geometry of the surrounding membranes or organelles and can behave differently, by forming "threads" that can snake around organic structures and affect the shape of large, folded polymers. Previous work with supercooled vicinal water shows that supercooling this type of water may makes membrane surfaces more pliable. See https://www-.sciencedirect.com/science/article/pii/0378437191903187.

With reference to FIGS. 3A-3B and 4, the microsurgical probe 120 may have a probe structure 126 that is configured to house one or more sperm 364. For example, the probe structure 126 may be configured as a hollow needle. The needle may have an inner cross-sectional shape that is circular, semicircular, or other shape that allows for this type of sperm harboring compartment. Additionally, the outer cross-sectional shape of the probe 120 as a hollow needle may be of any shape to support the probe accessory tools 160 or 360 and the probe's functional capabilities. Moreover, the outer-cross sectional shape may be constructed to house the piezoelectrical mechanisms employed to actuate the probe accessory tools 160 or 360. The cross-sectional shaped exterior may also be modified to cover receptacles that can hold the probe accessory tools 160 for storage until activated so that they do not interfere with other operations of the microsurgical probe 120.

Alternatively, an outermost cross-sectional shape that reduces the likelihood of bursting an older ovum 366 may cover receptacles for the probe accessory tools 160 or 360. For example, a wide, round, shape for the tip, with a slight concavity may facilitate entry into the oocyte membrane at a perpendicular angle. Such a shape may also facilitate application of suction to the ovum 366 in order to apply a protocol wherein suction of part of the ovum membrane may provide better conditions for successful ICSI as determined by the AI system. An embodiment that employs an oval and angled probe may also facilitate direct injection of the sperm 364 into the ovum 366 over a traditionally configured needle.

Additional embodiments for the microsurgical probe 120 may be configured as hollow microneedles on the order of 21 gauge (0.819 mm) and submillimeter needles. The needles may be angled or beveled to facilitate penetration of the oocyte membrane (an oocyte is about 110-120 μm). The hollow portion of the needle may also be configured and shaped to ensure the easy injection of the sperm cell (a sperm cell is about 50 μm). Embodiments for needle shapes may be considered in terms of least amount of trauma to the target ovum 366. Examples of some of these needle shapes may be found at https://www.ncbi.nlm.nih.gov/pmc/articles/PMC2769648/, and https://unionmedico.com/expanded-needle-and-syringe-guide/. The shapes discussed in these examples range from round needle apertures to diagonally angled. And, the external casing includes beveled, round, and trapezoidal. Because of their very small size, microfabrication methods that have been adapted from the microelectronics industry may be employed to produce these microneedles. Some embodiments of these needles may be microfabricated from nickel and silicon.

The sperm 364 may be collected and selected in any conventional manner. Alternatively, the sperm may be selected in accordance with one or more of the techniques disclosed in U.S. Prov. Pat. Appl. No. 62/827,199, which was filed on Apr. 1, 2019, and U.S. patent application Ser. No. 16/817,610, filed on Mar. 13, 2020. The contents of both of these patent applications are herein incorporated by reference in their entirety for all purposes. The tail of the sperm 364 may remain intact, especially if the sperm 364 is intended to be released to swim freely through a puncture made in the ovum 366. However, for procedures where the sperm 364 is to be released inside the ovum 366, then the tail of the sperm 364 may be cut off to facilitate immobilization.

With the sperm 364 positioned in the microsurgical probe 120, the software processing system may employ light emitted from the optical fiber 130 and data from one or more sensors 152 to guide the microsurgical probe 120, through the use of controllers, into a desirable position in proximity to an ovum 366. In a process step 400, the software processing system may control the delivery of a pre-penetration chemical 142 through the chemical feed path 134 at a suitable concentration, volume, and delivery rate and force. The pre-penetration chemical may include a softening agent and/or an ovum-encapsulation chemical, such as previously described.

In a process step 402, the softening or encapsulation chemical 142 may spread to form a thin layer to envelop the ovum 366. In a process step 406, an image database (which may include images of past procedures) and data from current sensors 152 may be supplied to the software processing system (which may include an AI system) to employ deep learning to cross-correlate the data in a process step 408 to ultimately determine (in a process step 410) whether the periphery of the ovum 366 is sufficiently lubricated for press testing the ovum membrane. One method for determining adequate lubrication may involve evaluation of lubrication thickness by way of a visual sensor, as previously described. The software processing system may implement a feedback loop until a state of adequate ovum lubrication is established.

In a process step 404, the software processing system can utilize the cross-correlation deep learning process 408 in conjunction with sensor data and historical data to identify potential sperm injection points on the surface of the ovum 366. Similarly, the software processing system may determine the most appropriate time and manner to test and evaluate the potential sperm injection points in connection with process steps 404 and 410. Testing may involve vibration provided by the resonator motor 150, such as a piezoelectric actuator. In one embodiment, a visual sensor 150, such as a camera, may be aligned so as to detect vibration of the membrane. An algorithm can be run with this visual sensor 150 to detect for changes in resonance of the membrane. Changes in resonance may indicate where the membrane is more turgid or more flaccid. In particular, increases in resonance may imply more turgor. In other examples of such testing, visual, chemical, and/or needle force feedback (such as measured by spring force and/or compression with respect to the probe accessory tools 360) may be compared to database references to determine the risk factors associated with penetrating the membrane of the ovum 366 at specific locations without bursting it. The concentration of the membrane-softening agent can be actively varied by the software processing system in response to the results gathered during test pressing or vibration testing of the ovum 366.

After establishing a preferred sperm injection point, in a process step 412, the software processing system can utilize the cross correlation deep learning process 408 in conjunction with sensor data and historical data to initiate a most desirable vibration from the resonator motor 150 at an identifiably suitable time and cause the microsurgical probe to penetrate the outer surface of the ovum 366 as shown in FIG. 3B. The concentration of the membrane-softening agent can be actively varied by the software processing system during the penetration procedure. Moreover, the software processing system may guide an injection needle controller to control the location and angle of injection, the rate and alternation of needle approach and retreat, the rate and modes of resonant vibration of the needle, and/or the rate of sperm injection.

In a process step 414, the probe tool 360 may be retracted under the guidance of the software processing system as informed by sensor data. If the probe tip is configured for entering the ovum 366, then the probe tip may be retracted under the guidance of the software processing system as informed by sensor data. Alternatively, if the oocyte membrane is to be partly sucked into the probe tip, then the probe accessory tools 360 may be extended and retracted as desirable to stabilize their orientation with regard to the membrane of the ovum 366 so as to not accidently tear the membrane (at a stabilization site away from the injection point) during the vacuum and injection procedure.

The sperm-coaxing actuator 362 may help drive the sperm 364 from the tip of the microsurgical probe 120. For example, if the sperm 364 has had its tail removed, then a syringe plunger moved by the sperm-coaxing actuator 362 may push from behind to deliver the sperm 364 into the ovum 366. The plunger mechanism may be particularly useful in embodiments where the probe tip is inserted into the ovum 366. If the membrane of the ovum 366 is partly sucked in, the membrane can be cut or simply suctioned until a portion fails, then the sperm 364 can simply swim in into the ovum 366. Similarly, in embodiments where the membrane is pierced by a probe accessory tool 360, the sperm 364 can simply swim in into the ovum 366. The sperm-coaxing actuator 362 may alternatively provide some other inducement like vibration to encourage the sperm 364 to leave its housing. The sperm cell can be guided into the ovum 366 more easily after it has been pierced or a failure region has been created.

The software processing system may evaluate whether a flash chill treatment may be desirable to help seal the puncture point after fertilization. If so, the software processing system can deliver a chemical freeze agent through the chemical feed path 134. One of the previously described freeze agents or other flash chill techniques may be employed.

In process steps 416 and 418, an intact fertilized ovum 366, now a zygote, may be transferred to a solution in which the softening agent or other process-related chemicals may be rinsed off and/or neutralized shortly after the fertilization is complete. Removal of these chemical may help prevent unwanted side effects on the embryo prior to implantation.

CONCLUSION

The terms and descriptions used above are set forth by way of illustration and example only and are not meant as limitations. Those skilled in the art will recognize that many variations, enhancements and modifications of the concepts described herein are possible without departing from the underlying principles of the invention. For example, skilled persons will appreciate that the subject matter of any sentence or paragraph can be combined with subject matter of some or all of the other sentences or paragraphs, except where such combinations are mutually exclusive. The scope of the invention should therefore be determined only by the following claims, claims presented in a continuation patent application, and equivalents to the foregoing claims.

The invention claimed is:

1. A method for fertilizing an ovum comprising:
   guiding a microsurgical probe in proximity to the ovum;
   pressure testing potential sperm injection points on the outer surface of the ovum for risk of bursting the ovum;
   vibrating the outer surface of the ovum;
   detecting changes in resonance of the ovum to evaluate for comparative turgidity or flaccidity of potential sperm injection points on the outer surface of the ovum;
   selecting a preferred penetration point from one of the potential sperm injection points for penetration of the outer surface of the ovum;
   penetrating the outer surface of the ovum at the preferred penetration point; and
   injecting a sperm into the ovum.

2. The method of claim 1, wherein the microsurgical probe comprises:
   an optional probe support structure;
   an optical fiber for providing a feed path for an emission wavelength from a wavelength emitter;
   a chemical feed path for delivering a chemical;
   a resonator motor; and
   a probe accessory tool.

3. The method of claim 1, further comprising:
   pretreating the ovum with a chemical, wherein the chemical comprises one or more of a lubricating chemical, a temperature-adjusting chemical, a membrane-softening agent, or a de-wormer.

4. The method of claim 1, wherein vibrating the ovum employs a resonator motor which comprises an adaptive resonator or an adaptively unbalanced resonator.

5. The method of claim 1, wherein the microsurgical probe comprises a grasping tool, a hollow needle, a semicircular hollow needle, or a sperm coaxing actuator.

6. The method of claim 1, further comprising:
   adjusting the temperature of the outer surface of the ovum.

7. The method of claim 1, further comprising:
   delivering an emission wavelength from the microsurgical probe, wherein the emission wavelength comprises light, UV light, visible light, infrared light, sound, audible sound, ultrasound, or a radio wave.

8. The method of claim 1, further comprising:
employing an image sensor or a sound sensor to evaluate potential injection points.

9. The method of claim 1, wherein the microsurgical probe comprises a flash chill tip.

10. The method of claim 3, further comprising;
distributing the chemical in a thin coat on the surface of the ovum.

11. The of claim 1 employing feedback control with respect to operation of the microsurgical probe.

12. The method of claim 1, wherein an artificial intelligence (AI) system employing one or more processors assists in operation of the microsurgical probe.

13. The method of claim 1, further comprising: determining when a trial press to a location along an outer surface of an ovum is least vulnerable to popping the ovum and determining when resonance has adequately allowed for a safe injection and subsequent removal.

14. The method of claim 1, wherein penetrating the outer surface of the ovum involves one or more of: penetrating an ovum older than 30 years old, penetrating an ovum that has a statistically greater susceptibility to popping than an average ovum, or penetrating an ovum having a coat that exhibits reduced flexibility, and involves one or more penetrating of an ovum that is a mammalian ovum, penetrating an ovum that is a horse ovum, or penetrating an ovum that is a human ovum.

15. The method of claim 1, further comprising:
employing an injection needle controller that controls one or more of the location and angle of injection, the rate and alternation of injection needle approach and retreat, the rate and modes of resonant vibration of the needle, and the rate of sperm injection.

16. The method of claim 1, further comprising:
rotating the ovum, loosening the ovum, or compressing the ovum as test sites for penetration are evaluated.

17. The method of claim 1, wherein force feedback data as measured by spring force and compression and visual data are compared to database references to determine degree of risk of ovum membrane popping.

18. The method of claim 1, wherein one or more functions associated with the microsurgical probe are activated or actuated by a piezoelectric actuator.

19. The method of claim 1, further comprising:
prior to pressure testing the ovum, supplying a softener to the outer surface of the ovum; and
evaluating thickness of the softener on the outer surface of the ovum.

20. The method of claim 19, further comprising:
visually determining with an image sensor whether the outer surface of the ovum is adequately lubricated.

21. The method of claim 1, further comprising:
selecting mode of vibration and timing for penetration of the outer surface of the ovum.

22. The method of claim 1, wherein injecting the sperm into the ovum employs a sperm-coaxing actuator positioned within the microsurgical probe.

23. The method of claim 1, further comprising:
employing a flash chill treatment to help seal a puncture at the preferred penetration point after sperm injection.

24. The method of claim 1, further comprising:
visually evaluating potential injection points on an outer surface of the ovum for risk of bursting the ovum.

* * * * *